[54] ALKANOIC ACID DERIVATIVES AND HERBICIDAL COMPOSITIONS

[75] Inventors: Koichiro Kaku, Shizuoka; Nobuhide Wada; Akira Takeuchi, both of Kakegawa; Yasufumi Toyokawa, Tokyo; Takeshige Miyazawa, Shizuoka; Ryo Yoshida, Shizuoka; Kazuhiko Sugiyama, Shizuoka, all of Japan

[73] Assignees: Kumiai Chemical Industry Co., Ltd.; Ihara Chemical Industry Co., Ltd., both of Tokyo, Japan

[21] Appl. No.: 571,118

[22] Filed: Aug. 23, 1990

Related U.S. Application Data

[62] Division of Ser. No. 368,808, Jun. 20, 1989, Pat. No. 4,968,340.

[30] Foreign Application Priority Data

Jun. 20, 1988 [JP] Japan .................. 63-150063

[51] Int. Cl.$^5$ .................. C07D 251/46; C07D 251/30; A01N 43/66
[52] U.S. Cl. ........................ 71/93; 544/194; 544/218; 544/213; 544/219; 544/211; 544/212; 71/90
[58] Field of Search ............ 71/90, 93; 544/211, 544/212, 219, 213, 194, 218

[56] References Cited

PUBLICATIONS

Levitt, Chemical Abstracts, vol. 95, entry 150714m (1981).

*Primary Examiner*—John M. Ford
*Attorney, Agent, or Firm*—Oblon, Spivak, McClelland, Maier & Neustadt

[57] ABSTRACT

A herbicidal alkanoic acid derivative of the formula:

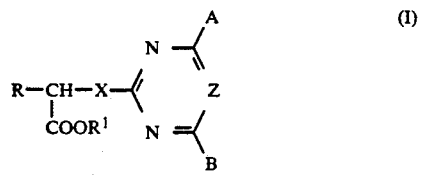

-continued

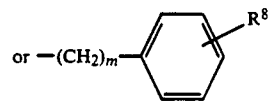

wherein $R^3$ is a hydrogen atom, a halogen atom, a halogen-substituted alkyl group, an alkyl group, a cycloalkyl group, an alkylthioalkyl group, a hydroxyalkyl group, a hydroxyl group, a cyano group, an acyloxyalkyl group, a thienyl group, a naphthyl group, a dihydronaphthyl group or $-(CH_2)_m-\underset{}{\underset{}{\bigcirc}}R^8$ wherein $R^8$ is a hydrogen atom, a halogen atom, a nitro group, an alkyl group, an alkoxy group or $-S(O)_nR^9$ wherein $R^9$ is an alkyl group, and n is an integer of from 0 to 2, m is an integer of from 0 to 2, each of $R^2$ and $R^4$ which may be the same or different is a hydrogen atom or an alkyl group, or $R^2$ and $R^4$ form together with the adjacent carbon atom a 3-, 4-, 5- or 6-membered ring which may contain an oxygen atom and may be substituted by one or two alkyl groups, each of $R^5$ and $R^6$ which may be the same or different is a hydrogen atom or an alkyl group, $R^7$ is an alkyl group or a phenyl group, or $R^6$ and $R^7$ form $-(CH_2)_l-$ wherein l is an integer of 3 or 4 which may be substituted by one or two alkyl groups, or R is an alkenyl group, a dihyronaphthyl group, a tetrahydronaphthyl group, a 1-oxo-1,2,3,4-tetrahydronaphthyl group, a 1,2-epoxycycloalkyl group or an indanyl group which may be substituted by an alkyl or alkoxy group; $R^1$ is a hydrogen atom, an alkyl group, an alkenyl group, an alkynyl group, a phenyl group, an alkylideneamino group, an alkoxyalkyl group, an alkoxycarbonylalkyl group, a halogen-substituted alkyl group, a cycloalkyl group, a nitro-substituted phenylthioalkyl group, a halogen atom or a benzyl group which may be substituted by an alkyl or alkoxy group; or R and $R^1$ form a ring; A is an alkyl group, an alkoxy group, an alkylthio group, a halogen atom, a halogen-substituted alkoxy group, an amino group, an alkylamino group or a dialkylamino group; B is a hydrogen atom, an alkyl group, an alkoxy group or a halogen-substituted alkoxy group; X is an oxygen atom or a sulfur atom; and Z is a methine group or a nitrogen atom; and a salt thereof.

9 Claims, No Drawings

ALKANOIC ACID DERIVATIVES AND HERBICIDAL COMPOSITIONS

This is a division of application Ser. No. 07/368,808, filed June 20, 1989, now U.S. Pat. No. 4,968,340.

The present invention relates to novel alkanoic acid derivatives and herbicidal compositions containing them, which are useful for application to paddy fields, and upland fields and non-agricultural fields.

In recent years, many herbicides have been developed and practically used, and they have contributed to the improvement of productivity and to energy saving for agricultural works.

For example, European Patent 262,393 discloses N-(1-cyano-1,2-dimethylpropyl)-2-pyrimidinyloxypropionamide. However, this is concerned with an agricultural fungicide. Further, German Laid-open Application No. 2,314,160 discloses 2-[4-chloro-6-(4-chlorobenzyl)aminopyrimidinyl]]thio propionic acid as a 2-pyrimidinylthio acetic acid derivative, which exhibits anticholesteremics.

However, such conventional herbicides have various problems with respect to the herbicidal effects and safety in their practical application. Therefore, it has been desired to develop a herbicide having improved herbicidal effects and safety to crop plants.

The present invention provides an alkanoic acid derivative of the formula:

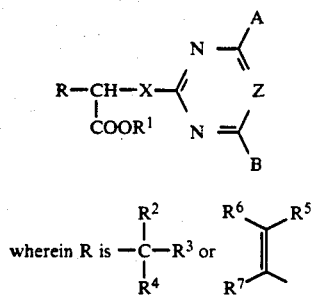

wherein $R^3$ is a hydrogen atom, a halogen atom, a halogen-substituted alkyl group, preferably a halogen-substituted $C_1$–$C_4$ alkyl group, an alkyl group, preferably a $C_1$–$C_{15}$ alkyl group, more preferably a $C_1$–$C_4$ alkyl group, a cycloalkyl group, preferably a $C_3$–$C_6$ cycloalkyl group, an alkylthioalkyl group, preferably a $C_1$–$C_4$ alkylthio-$C_1$–$C_4$ alkyl group, a hydroxyalkyl group, preferably a hydroxy-$C_1$–$C_4$ alkyl group, a hydroxyl group, a cyano group, an acyloxyalkyl group, preferably an acyloxy-$C_1$–$C_4$ alkyl group, a thienyl group, a naphthyl group, a dihydronaphthyl group or

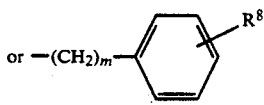

wherein $R^8$ is a hydrogen atom, a halogen atom, a nitro group, an alkyl group, preferably a $C_1$–$C_4$ alkyl group, an alkoxy group, preferably a $C_1$–$C_4$ alkoxy group or —$S(O)_nR^9$ wherein $R^9$ is an alkyl group, preferably a $C_1$–$C_4$ alkyl group, and n is an integer of from 0 to 2, m is an integer of from 0 to 2, each of $R^2$ and $R^4$ which may be the same or different is a hydrogen atom or an alkyl group, preferably a $C_1$–$C_4$ alkyl group, or $R^2$ and $R^4$ form together with the adjacent carbon atom a 3-, 4-, 5- or 6-membered ring which may contain an oxygen atom and may be substituted by one or two alkyl groups, preferably $C_1$–$C_4$ alkyl groups, each of $R^5$ and $R^6$ which may be the same or different is a hydrogen atom or an alkyl group, preferably a $C_1$–$C_4$ alkyl group, $R^7$ is an alkyl group, preferably a $C_1$–$C_4$ alkyl group, or a phenyl group, or $R^6$ and $R^7$ form —$(CH_2)_l$— wherein l is an integer of 3 or 4 which may be substituted by one or two alkyl groups, preferably $C_1$–$C_4$ alkyl groups, or R is an alkenyl group, preferably a $C_2$–$C_6$ alkenyl group, a dihydronaphthyl group, a tetrahydronaphthyl group, a 1-oxo-1,2,3,4-tetrahydronaphthyl group, a 1,2-epoxycycloalkyl group or an indanyl group which may be substituted by an alkyl or alkoxy group; $R^1$ is a hydrogen atom, an alkyl group, preferably a $C_1$–$C_4$ alkyl group, an alkenyl group, preferably a $C_2$–$C_6$ alkenyl group, an alkynyl group, preferably a $C_2$–$C_6$ alkynyl group, a phenyl group, an alkylideneamino group, an alkoxyalkyl group, preferably a $C_1$–$C_4$ alkoxy-$C_1$–$C_4$ alkyl group, an alkoxycarbonylalkyl group, preferably a $C_1$–$C_4$ alkoxycarbonyl-$C_1$–$C_4$ alkyl group, a halogen-substituted alkyl group, preferably a halogen-substituted-$C_1$–$C_4$ alkyl group, a cycloalkyl group, preferably a $C_3$–$C_5$ cycloalkyl group, a nitro-substituted phenylthioalkyl group, preferably a nitro-substituted phenylthio-$C_1$–$C_4$ alkyl group, a halogen atom or a benzyl group which may be substituted by an alkyl, preferably $C_1$–$C_4$ alkyl, or alkoxy, preferably $C_1$–$C_4$ alkoxy group; or R and $R^1$ form a ring; A is an alkyl group, preferably a $C_1$–$C_4$ alkyl group, an alkoxy group, preferably a $C_1$–$C_4$ alkoxy group, an alkylthio group, preferably a $C_1$–$C_4$ alkylthio group, a halogen atom, a halogen-substituted alkoxy group, preferably a halogen-substituted $C_1$–$C_4$ alkoxy group, an amino group, an alkylamino group, preferably a $C_1$–$C_4$ alkylamino group, or a dialkylamino group, preferably a di-$C_1$–$C_4$ alkylamino group; B is a hydrogen atom, an alkyl group, preferably a $C_1$–$C_4$ alkyl group, an alkoxy group, preferably a $C_1$–$C_4$ alkoxy group, or a halogen-substituted alkoxy group, preferably a halogen-substituted $C_1$–$C_4$ alkoxy group; X is an oxygen atom or a sulfur atom; and Z is a methine group or a nitrogen atom; and a salt thereof.

The present invention also provides a herbicidal composition comprising a herbicidally effective amount of the alkanoic acid derivative of the formula I or a salt thereof, and an agricultural adjuvant.

Further, the present invention provides a method for killing weeds which comprises applying a herbicidally effective amount of the alkanoic acid derivative of the formula I or a salt thereof to a locus to be protected.

Now, the present invention will be described in detail with reference to the preferred embodiments.

In the formula I, R is preferably a straight chain or branched alkyl group, a cycloalkyl group or

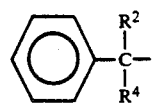

wherein each of $R^2$ and $R^4$ which may be the same or different is a hydrogen atom or an alkyl group; $R^1$ is a hydrogen atom or an alkyl group; each of A and B which may be the same or different is an alkyl group, an alkoxy group or a dihaloalkoxy group; and X and Z are as defined above; and a salt thereof.

Preferably, each of A and B is a methoxy group. X is preferably an oxygen atom, and Z is preferably a methine group. In a preferred embodiment, R is a straight or branched $C_3$-$C_5$ alkyl group, a cyclopentyl group, an α-methylbenzyl group, or an α,α-dimethylbenyl group, $R_1$ is a hydrogen atom or a $C_1$-$C_4$ alkyl group; each of A and B which may be the same or different is an alkyl group or an alkoxy group; and X and Z are as defined above. In another preferred embodiment R is an isopropyl group, a tert-butyl group, a cyclopentyl group or an α,α-dimethylbenzyl group; $R^1$ is a hydrogen atom, a methyl group or an ethyl group; and X and Z are as defined above.

Among the compounds of the formula I, the following compounds show particularly good herbicidal activities. Namely, in the formula I, R is an isopropyl group, a secondary butyl group, a tert-butyl group, a cyclopentyl group or an α,α-dimethylbenzyl group, $R^1$ is a hydrogen atom or a $C_1$-$C_4$ alkyl group, A is a methyl group, a methoxy group, a halogen-substituted alkoxy group, a dihalogen-substituted alkoxy group, an amino group, alkylamino group or a dialkylamino group, and B is a methyl group or a methoxy group.

When both A and B are methyl groups, R is preferably a $C_3$-$C_5$ alkyl group.

The salt of the alkanoic acid derivative of the formula I may be an alkali metal salt, an alkaline earth metal salt, a transition metal salt, an ammonium salt or an organic ammonium salt. Particularly preferred is a isopropylamine salt, a dimethylamine salt, an ammonium salt, a sodium salt, a potassium salt or a calcium salt.

Now, typical examples of the compound of the formula I of the present invention will be presented in Table 1. Compound Nos. given in the Table will be referred to in the subsequent description in the specification.

TABLE 1

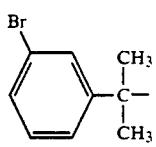

| Compound No. | R | $R^1$ | X | A | B | Z | Melting point (°C.) or refractive index ($n_D^{20}$) |
|---|---|---|---|---|---|---|---|
| 1 | $CH_3$ | $C_2H_5$ | O | $OCH_3$ | $OCH_3$ | CH | 1.4841 |
| 2 | $C_2H_5$ | " | " | " | " | " | 62~63 |
| 3 | " | H | " | " | " | " | 138~140 |
| 4 | i-$C_3H_7$ | " | " | " | " | " | 132~135 |
| 5 | n-$C_3H_7$ | $C_2H_5$ | " | " | " | " | 47~48 |
| 6 | " | H | " | " | " | " | 112~113 |
| 7 | n-$C_4H_9$ | " | " | " | " | " | 112~115 |
| 8 | " | $CH_3$ | " | " | " | " | 1.4868 |
| 9 | t-$C_4H_9$ | H | " | " | " | " | 182~184 |
| 10 | " | $CH_3$ | " | " | " | " | 97~105 |
| 11 | " | $C_2H_5$ | " | " | " | " | 98~99 |
| 12 | " | H | " | $CH_3$ | $CH_3$ | " | 167~169 |
| 13 | " | $CH_3$ | " | " | " | " | 1.4868 |
| 14 | " | " | " | " | $OCH_3$ | " | 1.4763 |
| 15 | " | H | " | " | " | " | Not measurable |
| 16 |  | $C_2H_5$ | " | $OCH_3$ | " | " | 116~120 |
| 17 | t-$C_4H_9$ | $CH_3$ | " | Cl | " | " | 1.5946 |
| 18 | i-$C_4H_9$ | H | " | $OCH_3$ | " | " | 117~119 |
| 19 | " | $C_2H_5$ | " | " | " | " | 1.4823 |
| 20 | sec-$C_4H_9$ | H | " | " | " | " | 92~96 |
| 21 | " | $C_2H_5$ | " | " | " | " | 1.4878 |
| 22 | n-$C_5H_{11}$ | H | " | " | " | " | 94~95 |
| 23 | " | $C_2H_5$ | " | " | " | " | 1.4769 |
| 24 | $C_2H_5$<br>$\|$<br>$C_2H_5CH-$ | H | " | " | " | " | 137~142 |
| 25 | " | $CH_3$ | " | " | " | " | 60~63 |
| 26 | " | $C_2H_5$ | " | " | " | " | 80~82 |
| 27 | " | $CH_2C{\equiv}CH$ | " | " | " | " | 88~89 |
| 28 | $C_2H_5$<br>$\|$<br>$C_2H_5CH-$ |  | O | $OCH_3$ | $OCH_3$ | CH | 95~96 |

TABLE 1-continued $$\text{R—CH—X}\underset{\text{COOR}^1}{\overset{}{\diagup}}\begin{array}{c}N=\overset{A}{C}\\ \phantom{N}\diagdown Z\\ N=\underset{B}{C}\end{array}$$

| Compound No. | R | R$^1$ | X | A | B | Z | Melting point (°C.) or refractive index (n$_D^{20}$) |
|---|---|---|---|---|---|---|---|
| 29 | CH$_3$–C$_3$H$_7$CH– | H | " | " | " | " | 109~114 |
| 30 | " | C$_2$H$_5$ | " | " | " | " | 1.4833 |
| 31 | CH$_3$CH=C$_2$H$_5$C– | H | " | " | " | " | 117~119 |
| 32 | CH$_3$C(C$_2$H$_5$)(C$_2$H$_5$)– | " | " | " | " | " | 156~159 |
| 33 | " | C$_2$H$_5$ | " | " | " | " | 84~87 |
| 34 | C$_6$H$_5$–C$_2$H$_4$C(CH$_3$)(CH$_3$)– | H | " | " | " | " | 100~102 |
| 35 | " | C$_2$H$_5$ | " | " | " | " | 87~88 |
| 36 | C$_6$H$_5$–CH(CH$_3$)– | H | " | " | " | " | 143~145 |
| 37 | " | C$_2$H$_5$ | " | " | " | " | 98~101 |
| 38 | C$_6$H$_5$–CH(C$_2$H$_5$)– | H | " | " | " | " | 145~150 |
| 39 | " | CH$_3$ | " | " | " | " | 77~80 |
| 40 | C$_6$H$_5$–CH(C$_3$H$_7$-i)– | H | " | " | " | " | Not measurable |
| 41 | " | CH$_3$ | " | " | " | " | 1.5224 |
| 42 | C$_6$H$_5$–C(CH$_3$)(CH$_3$)– | H | " | " | " | " | 163~165 |
| 43 | " | CH$_3$ | " | " | " | " | 95~97 |
| 44 | " | C$_2$H$_5$ | " | " | " | " | 123~124 |
| 45 | C$_6$H$_5$–C(CH$_3$)(CH$_3$)– | CH$_2$–C$_6$H$_5$ | O | OCH$_3$ | OCH$_3$ | CH | 115~116 |
| 46 | " | H | " | CH$_3$ | " | " | 152~154 |
| 47 | " | " | " | " | CH$_3$ | " | 115~117 |
| 48 | " | CH$_3$ | " | " | OCH$_3$ | " | 1.5310 |
| 49 | " | " | " | " | CH$_3$ | " | 1.5332 |

TABLE 1-continued $$R-CH-X-\underset{COOR^1}{\overset{}{|}}\underset{N}{\overset{N}{=}}\underset{B}{\overset{A}{\underset{Z}{\diamond}}}$$

| Compound No. | R | R¹ | X | A | B | Z | Melting point (°C.) or refractive index ($n_D^{20}$) |
|---|---|---|---|---|---|---|---|
| 50 | C₆H₅-C(CH₃)(C₂H₅)- | H | " | OCH₃ | OCH₃ | " | 140~147 |
| 51 | " | CH₃ | " | " | " | " | 112~116 |
| 52 | C₆H₅-C(C₂H₅)(C₂H₅)- | " | " | " | " | " | 1.5333 |
| 53 | 2-Cl-C₆H₄-C(CH₃)(CH₃)- | H | " | " | " | " | 208~215 |
| 54 | " | CH₃ | " | " | " | " | 140~143 |
| 55 | " | CH₂-C₆H₅ | " | " | " | " | 123~124 |
| 56 | " | CH₂-C₆H₄-OCH₃ | " | " | " | " | 128~130 |
| 57 | 3-Cl-C₆H₄-C(CH₃)(CH₃)- | H | " | " | " | " | 163~165 |
| 58 | " | CH₃ | " | " | " | " | 133~137 |
| 59 | " | C₄H₉-i | " | " | " | " | 85~86 |
| 60 | " | CH₂CH=CH₂ | " | " | " | " | 118~121 |
| 61 | " | Na | " | " | " | " | 220~226 |
| 62 | n-C₃H₇-C(CH₃)(CH₃)- | H | " | " | " | " | 126~127 |
| 63 | n-C₃H₇-C(CH₃)(CH₃)- | CH₃ | O | OCH₃ | OCH₃ | CH | 63~65 |
| 64 | " | C₂H₅ | " | " | " | " | 71~73 |
| 65 | cyclopentyl | H | " | " | " | " | 140~144 |
| 66 | " | C₂H₅ | " | " | " | " | 55~56 |

TABLE 1-continued

R—CH—X—[triazine with N, A, B, Z]
   |
   COOR¹

| Compound No. | R | R¹ | X | A | B | Z | Melting point (°C.) or refractive index ($n_D^{20}$) |
|---|---|---|---|---|---|---|---|
| 67 |  cyclohexyl-CH₂— | H | " | " | " | " | 149~152 |
| 68 | " | C₂H₅ | " | " | " | " | 86~87 |
| 69 |  cyclopentenyl— | H | " | " | " | " | 145~148 |
| 70 | " | C₂H₅ | " | " | " | " | 73~74 |
| 71 |  cyclohexenyl— | H | " | " | " | " | 142~143 |
| 72 | " | CH₃ | " | " | " | " | 76~77 |
| 73 | " | C₂H₅ | " | " | " | " | 80~81 |
| 74 | 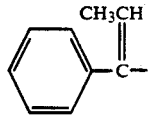 C₆H₅—C(=CHCH₃)— | H | " | " | " | " | 111~115 |
| 75 | " | C₂H₅ | " | " | " | " | 97~101 |
| 76 | CH₃—CH(OH)— | " | " | " | " | " | 1.4993 |
| 77 | HOCH₂C(CH₃)₂— | H | " | " | " | " | 104~110 |
| 78 | " | CH₃ | " | " | " | " | 80~92 |
| 79 | CH₃SC₂H₄— | " | " | " | " | " | 61~62 |
| 80 | CH₃COCH₂C(CH₃)₂— | H | O | OCH₃ | OCH₃ | CH | 133~140 |
| 81 | 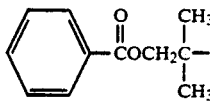 C₆H₅COCH₂C(CH₃)₂— | " | " | " | " | " | 69~75 |
| 82 |  2-methyl-1,3-dioxolan-2-yl— | C₂H₅ | " | " | " | " | 85~89 |
| 83 | 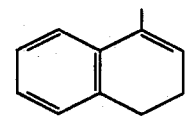 3,4-dihydronaphthalen-1-yl— | H | " | " | " | " | 169~173 |

TABLE 1-continued $$R-\underset{\underset{COOR^1}{|}}{CH}-X-\underset{N}{\overset{N}{=}}\underset{B}{\overset{A}{\underset{Z}{\diagup}}}$$

| Compound No. | R | R[1] | X | A | B | Z | Melting point (°C.) or refractive index ($n_D^{20}$) |
|---|---|---|---|---|---|---|---|
| 84 | " | C₂H₅ | " | " | " | " | 89~91 |
| 85 | C₆H₅-CH₂- | H | " | " | " | " | 135~137 |
| 86 | " | C₂H₅ | " | " | " | " | 59~60 |
| 87 | C₆H₅-C₂H₄- | H | " | " | " | " | 112~113 |
| 88 | " | C₂H₅ | " | " | " | " | 56~57 |
| 89 | C₆H₅-CH₂-C(CH₃)₂- | H | " | " | " | " | 107~111 |
| 90 | 4-Cl-C₆H₄-C(CH₃)₂- | " | " | " | " | " | 161~163 |
| 91 | " | C₂H₅ | " | " | " | " | 122.5~123.5 |
| 92 | " | CH₂-C₆H₄-Cl | " | " | " | " | 132~135 |
| 93 | 4-Br-C₆H₄-C(CH₃)₂- | H | " | " | " | " | 176~178 |
| 94 | 4-Br-C₆H₄-C(CH₃)₂- | C₂H₅ | O | OCH₃ | OCH₃ | CH | 133~135 |
| 95 | 2-CH₃-C₆H₄-C(CH₃)₂- | H | " | " | " | " | 183~190 |
| 96 | " | C₂H₅ | " | " | " | " | 116~119 |
| 97 | " | H.NH(i-C₃H₇)₂ | " | " | " | " | 152~157 |
| 98 | 3-CH₃-C₆H₄-C(CH₃)₂- | H | " | " | " | " | 157~159 |

TABLE 1-continued $$R-CH-X-\underset{COOR^1}{\overset{}{|}}\underset{N}{\overset{N}{=}}\underset{B}{\overset{A}{\underset{}{\bigcirc}}}Z$$

| Compound No. | R | R¹ | X | A | B | Z | Melting point (°C.) or refractive index ($n_D^{20}$) |
|---|---|---|---|---|---|---|---|
| 99 | " | CH₃ | " | " | " | " | 126~127 |
| 100 | " | H | " | CH₃ | " | " | 195~197 |
| 101 | " | CH₂C≡CH | " | OCH₃ | " | " | 95~97 |
| 102 | " | (2-Cl-benzyl: CH₂-C₆H₄-Cl) | " | " | " | " | 119~122 |
| 103 | CH₃-C₆H₄-C(CH₃)₂- | H | " | " | " | " | 155~157 |
| 104 | " | CH₃ | " | " | " | " | 115~117 |
| 105 | CH₃O-C₆H₄-C(CH₃)₂- | H | " | " | " | " | 158~160 |
| 106 | " | CH₃ | " | " | " | " | 104~106 |
| 107 | O₂N-C₆H₄-C(CH₃)₂- | H | " | " | " | " | 196~200 |
| 108 | " | CH₃ | " | " | " | " | 170~173 |
| 109 | CH₃S-C₆H₄-C(CH₃)₂- | H | " | " | " | " | 175~183 |
| 110 | " | CH₃ | " | " | " | " | 110~115 |
| 111 | CH₃S(O)-C₆H₄-C(CH₃)₂- | H | O | OCH₃ | OCH₃ | CH | 166~170 |
| 112 | " | CH₃ | " | " | " | " | 143~149 |
| 113 | CH₃SO₂-C₆H₄-C(CH₃)₂- | H | " | " | " | " | 213~216 |
| 114 | " | CH₃ | " | " | " | " | 143~144 |

TABLE 1-continued $$\underset{\underset{COOR^1}{|}}{R-CH-X}\diagup\!\!\!\!\diagdown\underset{N}{\overset{N}{=}}\underset{B}{\overset{A}{\diagdown\!\!\!\!\diagup}}Z$$

| Compound No. | R | R¹ | X | A | B | Z | Melting point (°C.) or refractive index ($n_D^{20}$) |
|---|---|---|---|---|---|---|---|
| 115 | 1-(2-propyl)naphthyl | H | " | " | " | " | 205~207 |
| 116 | " | CH₃ | " | " | " | " | 180~181 |
| 117 | 2-(2-propyl)thienyl | H | " | " | " | " | 156~159 |
| 118 | " | CH₃ | " | " | " | " | 77~80 |
| 119 | 1-phenylcyclopentyl | H | " | " | " | " | 140~142 |
| 120 | " | CH₃ | " | " | " | " | 135~138 |
| 121 | CH₃CH(Cl)— | C₂H₅ | " | " | " | " | 63~71 |
| 122 | n-C₇H₁₅ | " | " | " | " | " | 1.4755 |
| 123 | n-C₈H₁₇ | " | " | " | " | " | 1.4739 |
| 124 | n-C₉H₁₉ | " | " | " | " | " | 1.4785 |
| 125 | n-C₁₀H₂₁ | " | " | " | " | " | 1.4779 |
| 126 | n-C₁₂H₂₅ | " | " | " | " | " | 1.4738 |
| 127 | n-C₇H₁₅ | H | " | " | " | " | 91~92 |
| 128 | n-C₈H₁₇ | " | " | " | " | " | 86~87 |
| 129 | n-C₉H₁₉ | " | " | " | " | " | 86~87 |
| 130 | n-C₁₀H₂₁ | " | " | " | " | " | 87~92 |
| 131 | n-C₁₂H₂₅ | " | " | " | " | " | 83~85 |
| 132 | cyclopentyl | C₂H₅ | S | OCH₃ | OCH₃ | CH | 1.5310 |
| 133 | " | H | " | " | " | " | 125~127 |
| 134 | 1-methylcyclopentyl | C₂H₅ | O | " | " | " | 97~98 |
| 135 | " | H | " | " | " | " | 128~132 |
| 136 | 1-phenylethyl | CH₃ | " | CH₃ | CH₃ | " | 79~82 |
| 137 | " | H | " | " | " | " | 183~185 |

TABLE 1-continued

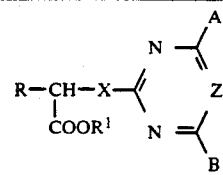

| Compound No. | R | R[1] | X | A | B | Z | Melting point (°C.) or refractive index ($n_D^{20}$) |
|---|---|---|---|---|---|---|---|
| 138 | (2-isopropylphenyl)-OCH₃ | CH₃ | " | OCH₃ | OCH₃ | " | 153~154 |
| 139 | " | H | " | " | " | " | 176~179 |
| 140 | 3-isopropylthiophene | CH₃ | " | " | " | " | 102~103 |
| 141 | " | H | " | " | " | " | 170~173 |
| 142 | C₂H₅C(CH₃)₂— | CH₃ | " | " | " | " | 72~73 |
| 143 | cyclopentyl-CH₂— | C₂H₅ | " | " | " | " | 1.4968 |
| 144 | " | H | " | " | " | " | 116~118 |
| 145 | n-C₁₄H₂₉ | C₂H₅ | " | " | " | " | 1.4769 |
| 146 | n-C₁₄H₂₉ | H | " | " | " | " | 83~85 |
| 147 | n-C₆H₁₃ | CH₃ | " | " | " | " | 54~56 |
| 148 | " | H | " | " | " | " | 107~115 |
| 149 | n-C₁₆H₃₃ | " | " | " | " | 1.4779 |  |
| 150 | " | H | " | " | " | " | 85~91 |
| 151 | C₆H₅C(CH₃)₂— | CH₃ | O | OCH₃ | OCH₃ | N | 85~87 |
| 152 | i-C₃H₇ | C₂H₅ | S | " | " | CH | 1.5162 |
| 153 | " | H | " | " | " | " | 76~78 |
| 154 | t-C₄H₉ | CH₃ | O | " | " | N | 1.4800 |
| 155 | NCC(CH₃)₂— | H | " | " | " | CH | 142~150 |
| 156 | C₂H₅CH(CH₃)— | C₂H₅ | S | " | " | " | 1.5168 |
| 157 | " | H | " | " | " | " | 82~87 |
| 158 | i-C₃H₇C(CH₃)₂— | CH₃ | O | " | " | " | 97~98 |
| 159 | " | H | " | " | " | " | 158~160 |

TABLE 1-continued

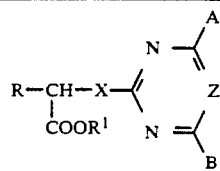

| Compound No. | R | R¹ | X | A | B | Z | Melting point (°C.) or refractive index ($n_D^{20}$) |
|---|---|---|---|---|---|---|---|
| 160 | CH₃—i-C₃H₇C— | C₂H₅ | " | " | " | " | 68~70 |
| 161 | " | H | " | " | " | " | 93~102 |
| 162 | cyclopentyl— | CH₃ | S | " | " | " | 1.5368 |
| 163 | t-C₄H₉ | " | O | OC₃H₇-i | " | " | 64~67 |
| 164 | " | " | " | OCHF₂ | CH₃ | " | 88~98 |
| 165 | " | H | " | OC₃H₇-i | OCH₃ | " | 135~140 |
| 166 | C₂H₅SO₂—C₆H₄—C(CH₃)₂— | CH₃ | " | OCH₃ | " | " | 90~92 |
| 167 | " | H | " | " | " | " | 187~190 |
| 168 | CH₃ | " | " | " | " | " | 154~156 |
| 169 | thienyl-CH₂— | " | " | " | " | " | 63~65 |
| 170 | methylcyclopentenyl- | H | O | OCH₃ | OCH₃ | CH | 125~130 |
| 171 | i-C₃H₇ | CH₃ | " | Cl | " | " | 1.4943 |
| 172 | " | H | " | " | " | " | 128~130 |
| 173 | C₆H₅—C(CH₃)₂— | CH₃ | " | OC₂H₅ | OC₂H₅ | " | 1.5219 |
| 174 | " | H | " | " | " | " | 144~148 |
| 175 | " | CH₃ | " | OC₃H₇-i | OC₃H₇-i | " | 96~98 |
| 176 | " | H | " | " | " | " | 165~170 |
| 177 | cyclopropyl-CH₂— | C₂H₅ | " | OCH₃ | OCH₃ | " | 1.4953 |
| 178 | " | H | " | " | " | " | 133~136 |
| 179 | CH₂=CH₃C— | C₂H₅ | " | " | " | " | 64~66 |
| 180 | " | H | " | " | " | " | 115~117 |
| 181 | CH₃—HOCH₂CH— | C₂H₅ | " | " | " | " | 1.5016 |

TABLE 1-continued

| Compound No. | R | R¹ | X | A | B | Z | Melting point (°C.) or refractive index ($n_D^{20}$) |
|---|---|---|---|---|---|---|---|
| 182 |  | CH₃ | " | " | CH₃ | " | 1.5033 |
| 183 | " | H | " | " | " | " | 138~143 |
| 184 | " | CH₃ | " | OCHF₂ | " | " | 1.4773 |
| 185 | " | H | " | " | " | " | 130~132 |
| 186 | " | CH₃ | " | OCH₃ | OCH₃ | N | 1.4998 |
| 187 | " | H | " | " | " | " | 1.4914 |
| 188 | " | CH₃ | S | CH₃ | CH₃ | CH | 1.5388 |
| 189 | " | H | " | " | " | " | 117~119 |
| 190 | " | i-C₃H₇ | O | OCH₃ | OCH₃ | " | 56~57 |
| 191 | " | n-C₄H₉ | " | " | " | " | 44~46 |
| 192 | 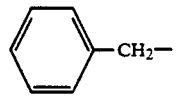 | 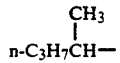 | O | OCH₃ | OCH₃ | CH | 83.5~85 |
| 193 | CH₃<br>n-C₃H₇CH— | C₂H₅ | S | " | " | " | 1.5140 |
| 194 | " | H | " | " | " | " | 63~67 |
| 195 | n-C₃H₇ | C₂H₅ | " | CH₃ | CH₃ | " | 1.5140 |
| 196 | " | H | " | " | " | " | 1.5368 |
| 197 | n-C₄H₉ | CH₃ | " | " | " | " | 1.5148 |
| 198 | " | H | " | " | " | " | 1.5306 |
| 199 | " | CH₃ | O | " | " | " | 1.4814 |
| 200 | " | H | " | " | " | " | 1.4949 |
| 201 | 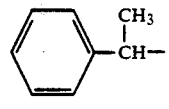 | CH₃ | " | OCH₃ | " | N | 1.5190 |
| 202 | t-C₄H₉ | H | " | Cl | " | CH | 30~35 |
| 203 | " | " | " | OC₂H₅ | " | " | 150~155 |
| 204 | " | " | " | OC₃H₇-n | " | " | 81~85 |
| 205 | " | CH₃ | " | OC₂H₅ | OC₂H₅ | " | 1.4783 |
| 206 | " | H | " | " | " | " | 155~157 |
| 207 | " | CH₃ | " | OC₃H₇-i | OC₃H₇-i | " | 1.4722 |
| 208 | " | H | " | " | " | " | 147~150 |
| 209 | " | " | " | OCH₃ | OC₂H₅ | " | 78~83 |
| 210 | CH₃<br>s-C₄H₉CH— | C₂H₅ | O | " | OCH₃ | " | 1.4812 |
| 211 | " | H | " | " | " | " | 162~167 |
| 212 | 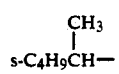 | CH₃ | " | CH₃ | CH₃ | " | 1.5013 |
| 213 | " | H | " | " | " | " | 130~134 |
| 214 |  | H | " | OCH₃ | OCH₃ | " | 180~183 |

TABLE 1-continued

| Compound No. | R | R¹ | X | A | B | Z | Melting point (°C.) or refractive index ($n_D^{20}$) |
|---|---|---|---|---|---|---|---|
| 215 | CH₃-C(C₂H₅)(CH₃)- | C₂H₅ | O | OCH₃ | OCH₃ | CH | 77~79 |
| 216 | " | H | " | " | " | " | 145~147 |
| 217 | C₆H₅-CH(CH₃)- | CH₃ | " | " | CH₃ | " | 1.5304 |
| 218 | " | H | " | " | " | " | 150~152 |
| 219 | cyclopentyl | CH₃ | " | " | OCH₃ | " | 64~66 |
| 220 | " | H | " | Cl | " | " | 135~140 |
| 221 | C₆H₅-C(CH₃)₂- | CH₃ | " | " | CH₃ | " | 75~88 |
| 222 | t-C₄H₉ | " | " | " | " | " | 1.4962 |
| 223 | 4-F-C₆H₄-C(CH₃)₂- | CH₃ | " | OCH₃ | OCH₃ | " | 120~122.5 |
| 224 | " | H | " | " | " | " | 175~178 |
| 225 | 2-F-C₆H₄-C(CH₃)₂- | CH₃ | " | " | " | " | 133~136 |
| 226 | " | H | " | " | " | " | 198~204 |
| 227 | cyclopentyl | C₂H₅ | " | Cl | " | " | 1.5085 |
| 228 | " | CH₃ | " | " | CH₃ | " | 1.5100 |
| 229 | C₆H₅-CH(CH₃)- | " | " | " | " | " | 1.5343 |
| 230 | 2-naphthyl-C(CH₃)₂- | " | " | OCH₃ | OCH₃ | " | 150~152 |

TABLE 1-continued
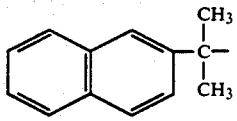
| Compound No. | R | R¹ | X | A | B | Z | Melting point (°C.) or refractive index ($n_D^{20}$) |
|---|---|---|---|---|---|---|---|
| 231 | 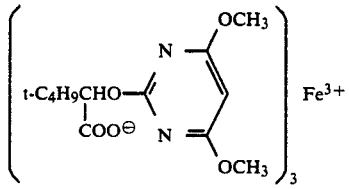 | H | O | OCH₃ | OCH₃ | CH | 162~166 |
| 232 | n-C₄H₉ | CH₃ | S | " | " | " | 1.5151 |
| 233 | " | H | " | " | " | " | 1.5258 |
| 234 | t-C₄H₉ | " | O | Cl | " | " | 56~67 |
| 235 | " | CH₃ | " | CH₃ | " | N | 1.4755 |
| 236 | " | " | " | OC₂H₅ | " | CH | 1.4794 |
| 237 | i-C₃H₇ | " | " | CH₃ | CH₃ | " | 1.4855 |
| 238 | " | H | " | " | " | " | 120~122 |
| 239 | " | CH₃ | " | " | OCH₃ | " | 1.4843 |
| 240 | " | H | " | " | " | " | 127~130 |
| 241 | " | CH₃ | " | Cl | CH₃ | " | 1.4923 |
| 242 | " | " | " | CH₃ | OCH₃ | N | 1.4765 |
| 243 | " | " | " | OCH₃ | " | CH | 57~58 |
| 244 | 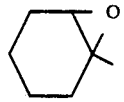 | | | | | | 178~181 |
| 245 | 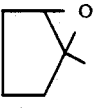 | C₂H₅ | O | OCH₃ | OCH₃ | CH | 108~110 |
| 246 | 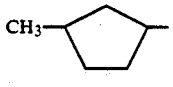 | " | " | " | " | " | 80~83 |
| 247 | 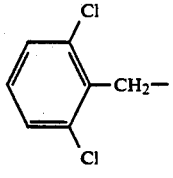 | " | " | " | " | " | 39~43 |
| 248 | " | H | " | " | " | " | 117~119 |
| 249 | 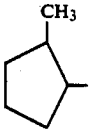 | " | " | " | " | " | 155~158 |
| 250 |  | C₂H₅ | O | OCH₃ | OCH₃ | CH | 92~95 |
| 251 | " | H | " | " | " | " | 118~120 |
| 252 | " | C₂H₅ | S | " | " | " | 1.5288 |
| 253 | " | H | " | " | " | " | 76~78 |

TABLE 1-continued $$R-CH-X-\underset{COOR^1}{\overset{}{|}} \begin{array}{c} N \diagup A \\ \diagdown Z \\ N \diagdown B \end{array}$$

| Compound No. | R | $R^1$ | X | A | B | Z | Melting point (°C.) or refractive index ($n_D^{20}$) |
|---|---|---|---|---|---|---|---|
| 254 | (methylcyclopentyl) | $C_2H_5$ | " | " | " | " | 1.5260 |
| 255 | " | H | " | " | " | " | 84~86 |
| 256 | $CH_3$ | " | " | " | " | " | 109~111 |
| 257 | (2,6-dichlorobenzyl)-$CH_2-$ | $C_2H_5$ | O | " | " | " | 130~132 |
| 258 | (2,6-dimethylbenzyl)-$CH_2-$ | H | " | " | " | " | 162~164 |
| 259 | $t$-$C_4H_9-$ | $CH_3$ | " | " | $OCHF_2$ | " | 62~70 |
| 260 | " | H | " | " | " | " | 149~153 |
| 261 | (cumyl, $C(CH_3)_2$-Ph) | " | " | Cl | $OCH_3$ | " | 163~168 |
| 262 | " | $CH_3$ | " | $OCH_3$ | $OCHF_2$ | " | 1.5081 |
| 263 | " | H | " | " | " | " | 147~149 |
| 264 | (cumyl) | $CH_3$ | O | $OCHF_2$ | $CH_3$ | CH | 1.5121 |
| 265 | (dimethylcyclopentyl) | $C_2H_5$ | " | $OCH_3$ | $OCH_3$ | " | 84~89 |
| 266 | " | H | " | " | " | " | 109~112 |
| 267 | $C_3H_7-$ | $C_2H_5$ | S | " | " | " | 1.5122 |
| 268 | " | H | " | " | " | " | 95~97 |
| 269 | (cumyl) | $CH_3$ | O | $OC_2H_5$ | $OC_2H_5$ | " | 67~68 |
| 270 | " | H | " | " | " | " | 145~148 |
| 271 | " | " | " | $OCH_3$ | $OC_3H_7$-i | " | 118~125 |

TABLE 1-continued

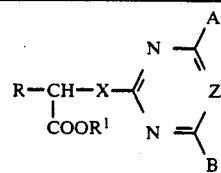

| Compound No. | R | R¹ | X | A | B | Z | Melting point (°C.) or refractive index ($n_D^{20}$) |
|---|---|---|---|---|---|---|---|
| 272 | (2,6-dimethylbenzyl) CH₃-C₆H₃(CH₃)-CH₂- | C₂H₅ | " | " | OCH₃ | " | 112~113 |
| 273 | (2-methylbenzyl) CH₃-C₆H₄-CH₂- | H | " | " | " | " | 176~180 |
| 274 | " | C₂H₅ | " | " | " | " | 63~65 |
| 275 | (2,4-dichloro-α,α-dimethylbenzyl) Cl₂C₆H₃-C(CH₃)₂- | CH₃ | " | " | " | " | 120~121 |
| 276 | " | H | " | " | " | " | 187~189 |
| 277 | (2-methyl-α-methylbenzyl) CH₃-C₆H₄-CH(CH₃)- | CH₃ | O | OCH₃ | OCH₃ | CH | 98~99 |
| 278 | (2-methyl-α-methylbenzyl) CH₃-C₆H₄-CH(CH₃)- | H | O | OCH₃ | OCH₃ | CH | 138~141 |
| 279 | (2,4-dimethylcyclopentyl) | C₂H₅ | S | " | " | " | 1.5202 |
| 280 | " | H | " | " | " | " | 1.5283 |
| 281 | (cyclopentyl) | C₃H₇-i | " | " | " | " | 1.5245 |
| 282 | " | -CH₂-C₆H₅ | " | " | " | " | 1.5633 |
| 283 | (2,4-dichloro-α,α-dimethylbenzyl) Cl₂C₆H₃-C(CH₃)₂- | CH₃ | O | " | " | " | 116~119 |

TABLE 1-continued

R—CH—X—[pyrimidine with A, B, Z, N]
|
COOR¹

| Compound No. | R | R¹ | X | A | B | Z | Melting point (°C.) or refractive index ($n_D^{20}$) |
|---|---|---|---|---|---|---|---|
| 284 | " | H | " | " | " | " | 165~167 |
| 285 | 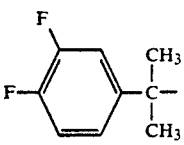 3,4-difluoro-α,α-dimethylbenzyl | CH₃ | " | " | " | " | 114~115 |
| 286 | " | H | " | " | " | " | 161~163 |
| 287 | 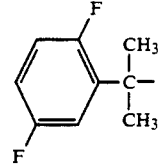 2,5-difluoro-α,α-dimethylbenzyl | CH₃ | " | " | " | " | 159~160 |
| 288 | " | H | " | " | " | " | 184~186 |
| 289 | 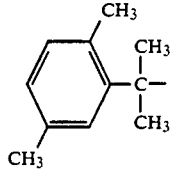 2,5-dimethyl-α,α-dimethylbenzyl | CH₃ | " | " | " | " | 132~136 |
| 290 | " | H | " | " | " | " | 185~187 |
| 291 |  cyclopentyl | C₄H₉ | S | OCH₃ | OCH₃ | CH | 1.5217 |
| 292 | " | CH₂C≡CH | " | " | " | " | 102~103 |
| 293 | 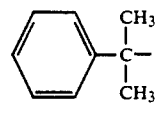 α,α-dimethylbenzyl | CH₃ | O | Cl | C₃H₇-i | " | 1.5255 |
| 294 | " | " | " | OCH₃ | " | " | 1.5252 |
| 295 | " | H | " | " | " | " | Not measurable |
| 296 | t-C₄H₉ | " | " | " | " | " | Not measurable |
| 297 | 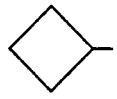 cyclobutyl | CH₃ | " | " | OCH₃ | " | 101~103 |
| 298 | " | H | " | " | " | " | 151~153 |
| 299 | " | CH₃ | S | " | " | " | 1.5389 |
| 300 | " | H | " | " | " | " | 131~133 |
| 301 | t-C₄H₉ | CH₃ | O | " | C₂H₅ | " | 1.4864 |
| 302 | " | H | " | " | " | " | 63~67 |
| 303 | 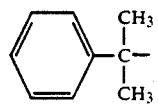 α,α-dimethylbenzyl | " | " | " | " | " | Not measurable |

TABLE 1-continued

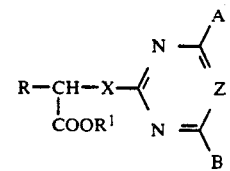

| Compound No. | R | R¹ | X | A | B | Z | Melting point (°C.) or refractive index ($n_D^{20}$) |
|---|---|---|---|---|---|---|---|
| 304 | 2,6-di(C₂H₅)-benzyl (CH₂-C₆H₃(C₂H₅)₂) | " | " | " | $OCH_3$ | " | 117~119 |
| 305 | " | $C_2H_5$ | " | " | " | " | 1.5222 |
| 306 | 2-CF₃-4-(C(CH₃)₂)-phenyl | $CH_3$ | " | " | " | " | 121~123 |
| 307 | 3-CF₃-, C(CH₃)₂-phenyl | H | O | $OCH_3$ | $OCH_3$ | CH | 175~177 |
| 308 | 3-F-, C(CH₃)₂-phenyl | $CH_3$ | " | " | " | " | 93~94 |
| 309 | " | H | " | " | " | " | 162~164 |
| 310 | 3-CH₃O-, C(CH₃)₂-phenyl | " | " | " | " | " | 160~164 |
| 311 | cyclopentyl | $C_2H_5$ | " | " | $OCHF_2$ | " | 1.4777 |
| 312 | " | H | " | " | " | " | 132~133 |
| 313 | cyclobutyl | $C_2H_5$ | " | " | $OCH_3$ | " | 71~73 |
| 314 | " | " | S | " | " | " | 1.5313 |
| 315 | $t\text{-}C_4H_9$ | H | " | " | " | " | 115~119 |
| 316 | cyclopentyl | $C_4H_9-S$ | " | " | " | " | 1.5231 |

TABLE 1-continued $$R-\underset{\underset{COOR^1}{|}}{CH}-X-\underset{N}{\overset{N}{\diagup}}\diagdown\underset{B}{\overset{A}{\diagdown}}Z$$

| Compound No. | R | R[1] | X | A | B | Z | Melting point (°C.) or refractive index ($n_D^{20}$) |
|---|---|---|---|---|---|---|---|
| 317 | " | CH(CH₃)(C₆H₅) | " | " | " | " | 1.5569 |
| 318 | cyclopentenyl | C₂H₅ | " | " | " | " | 1.5482 |
| 319 | " | H | " | " | " | " | 138~140 |
| 320 | cyclopentyl-CH₂— | C₂H₅ | " | " | " | " | 1.5270 |
| 321 | " | H | " | " | " | " | 95~98 |
| 322 | C₆H₅-C(CH₃)₂— | H | S | OCH₃ | OCH₃ | CH | 146~150 |
| 323 | i-C₃H₇ | CH₃ | " | " | " | " | 1.5247 |
| 324 | " | CH₂C≡CH | " | " | " | " | 1.5236 |
| 325 | t-C₄H₉ | H | " | CH₃ | CH₃ | " | 122~125 |
| 326 | " | " | " | OCH₃ | OCH₃ | N | 94~98 |
| 327 | cyclopentyl | CH(CH₃)(C₃H₇) | " | " | " | CH | 1.5190 |
| 328 | " | CH(C₂H₅)₂ | " | " | " | " | 1.5199 |
| 329 | " | C₂H₅ | " | " | " | N | 1.5304 |
| 330 | i-C₃H₇ | CH₃ | " | " | " | " | 1.5106 |
| 331 | " | H | " | " | " | " | 1.5240 |
| 332 | " | " | " | Cl | " | CH | 100~105 |
| 333 | " | " | " | CH₃ | CH₃ | " | 93~95 |
| 334 | " | CH₃ | " | Cl | OCH₃ | " | 1.5335 |
| 335 | " | C₂H₅ | " | CH₃ | CH₃ | " | 1.5152 |
| 336 | t-C₄H₉ | H | O | OCH₃ | OCH₃ | N | 37~40 |
| 337 | " | CH₂C₆H₅ | " | " | " | " | 63~66 |
| 338 | C₆H₅-C(CH₃)₂— | H | " | " | " | " | 41~44 |
| 339 | C₆H₅-C(CH₃)₂— | H | S | CH₃ | CH₃ | CH | 153~157 |
| 340 | " | " | " | OCH₃ | OCH₃ | N | 115~118 |
| 341 | t-C₄H₉ | H | " | " | OCHF₂ | CH | 95~100 |

TABLE 1-continued $$R-CH-X-\overset{N=A}{\underset{N=B}{\overset{|}{C}}}Z$$
$$\phantom{R-CH-X}COOR^1$$

| Compound No. | R | R¹ | X | A | B | Z | Melting point (°C.) or refractive index ($n_D^{20}$) |
|---|---|---|---|---|---|---|---|
| 342 | cyclobutyl | C₃H₇-i | " | " | OCH₃ | " | 1.5230 |
| 343 | cyclopentyl | H | " | " | " | N | 106~110 |
| 344 | " | C₂H₅ | " | Cl | " | CH | 1.5440 |
| 345 | " | H | " | " | " | " | 90~97 |
| 346 | " | C₂H₅ | " | CH₃ | " | " | 1.5327 |
| 347 | " | H | " | " | " | " | 91~93 |
| 348 | " | " | " | OCH₃ | OCHF₂ | " | 127~130 |
| 349 | " | C₂H₅ | " | " | " | " | 1.5064 |
| 350 | α,α-dimethylbenzyl | H | " | " | " | " | 136~140 |
| 351 | " | " | " | Cl | OCH₃ | " | 177~181 |
| 352 | t-C₄H₉ | " | " | " | " | " | 121~123 |
| 353 | C₂H₅ | " | " | OCH₃ | " | " | 82~83 |
| 354 | i-C₃H₇ | " | " | " | OCHF₂ | " | 85~88 |
| 355 | i-C₃H₇ | H | S | CH₃ | OCH₃ | CH | 1.5331 |
| 356 | Ph(CH₂)₃— | CH₃ | O | OCH₃ | " | " | 1.5343 |
| 357 | t-C₄H₉ | H | " | OCH₃ | H | " | Not measurable |
| 358 | " | " | " | N(CH₃)₂ | OCH₃ | " | 73~78 |
| 359 | " | " | " | SCH₃ | " | " | 150~158 |
| 360 | " | " | " | " | CH₃ | " | 194~200 |
| 361 | " | " | " | NHCH₃ | OCH₃ | " | 101~104 |
| 362 | " | " | " | OCHF₂ | OCHF₂ | " | 205~213 |
| 363 | " | " | S | NHCH₃ | OCH₃ | " | 124~127 |
| 364 | " | " | " | NHC₄H₉-t | " | " | 123~125 |
| 365 | α,α-dimethylbenzyl | " | O | NHCH₃ | " | " | 105~109 |
| 366 | " | " | " | N(CH₃)₂ | " | " | 154~158 |
| 367 | " | " | " | SCH₃ | " | " | 156~158 |
| 368 | " | " | " | OCHF₂ | OCHF₂ | " | 193~197 |
| 369 | " | " | " | NH₂ | OCH₃ | " | 227~230 |
| 370 | 1-tetralinyl | H | O | OCH₃ | OCH₃ | CH | 144~146 |
| 371 | " | CH₃ | " | " | " | " | 132~134 |
| 372 | CH₂=CH—CH₂— | H | " | " | " | " | 105~111 |

TABLE 1-continued
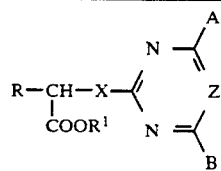
| Compound No. | R | R¹ | X | A | B | Z | Melting point (°C.) or refractive index ($n_D^{20}$) |
|---|---|---|---|---|---|---|---|
| 373 | (indanyl) | " | " | " | " | " | 113~117 |
| 374 | " | CH₃ | " | " | " | " | 93~96 |
| 375 | " | C₂H₅ | " | " | " | " | 187~189 |
| 376 | (CH₃)(CF₃)CH— | H | " | " | " | " | 112~114 |
| 377 | " | CH₃ | " | " | " | " | 62~64 |
| 378 | " | C₂H₅ | " | " | " | " | 52~54 |
| 379 | (2-methyl-tetralone) | " | " | " | " | " | Not measurable |
| 380 | (indanyl) | H | S | " | " | " | 112~115 |
| 381 | " | C₂H₅ | " | " | " | " | 71~73 |
| 382 | (1-methylindanyl) | " | O | " | " | " | 112~115 |
| 383 | (2-methylindanyl) | H | " | " | " | " | 148~151 |
| 384 | HOOC-C(CH₃)₂-CH₂— | H | " | " | " | " | 158~163 |
| 385 | (cyclopentyl) | —CH₂COC₂H₅ (with C=O) | O | OCH₃ | OCH₃ | CH | 84~85 |
| 386 | " | (phenyl) | " | " | " | " | 112~114 |

TABLE 1-continued

| Compound No. | R | R¹ | X | A | B | Z | Melting point (°C.) or refractive index ($n_D^{20}$) |
|---|---|---|---|---|---|---|---|
| 387 | " | −N=C(CH₃)₂ | " | " | " | " | 1.5162 |
| 388 | " | −CH₂S−C₆H₄−NO₂ | " | " | " | CH | 68~70 |
| 389 | " | −CH₂OCH₃ | " | " | " | " | 36~38 |
| 390 | " | −N=C(CH₃)₂ | S | " | " | " | 1.5452 |
| 391 | " | −CH₂S−C₆H₄−NO₂ | " | " | " | " | 1.6027 |
| 392 | " | CH₂OCH₃ | " | " | " | " | 1.5309 |
| 393 | " | C₆H₅ | " | " | " | " | 40~45 |
| 394 | " | −CH(CH₃)(CF₃) | " | " | " | " | 1.4958 |
| 395 | " | cyclopentyl | " | " | " | " | 1.5368 |
| 396 | 6-methyl-1-methylindanyl | CH₃ | O | " | " | " | 105~107 |
| 397 | " | H | " | " | " | " | 163~165 |
| 398 | n-C₃H₇ | " | S | " | " | N | 1.5301 |
| 399 | n-C₄H₉ | " | " | " | " | " | 1.5263 |
| 400 | t-C₄H₉ | " | " | " | CH₃ | " | 128~133 |
| 401 | C₆H₅C(CH₃)₂− | " | " | " | " | " | 46~49 |
| 402 | phenylcyclopropyl | H | O | OCH₃ | OCH₃ | CH | 115~120 |

TABLE 1-continued $$R-\underset{\underset{COOR^1}{|}}{CH}-X-\underset{\underset{B}{\overset{N=}{\diagdown}}}{\overset{N=A}{\diagup}}Z$$

| Compound No. | R | $R^1$ | X | A | B | Z | Melting point (°C.) or refractive index ($n_D^{20}$) |
|---|---|---|---|---|---|---|---|
| 403 | 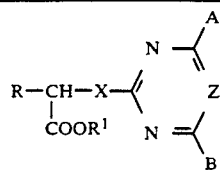 | " | " | " | " | " | 215~218 |
| 404 | " | CH₃ | " | " | " | " | 95~97 |
| 405 | t-C₄H₉ | H | S | N(CH₃)₂ | " | " | 105~110 |
| 406 | CH₃\\CH—/C₂H₅ | " | " | " | OCH₃ | " | N | 75~78 |
| 407 | t-C₄H₉ | " | " | " | NHCH₃ | " | " | 1.5187 |
| 408 | " | " | " | " | NHC₂H₅ | " | " | 51~55 |
| 409 | " | " | " | " | NH—C₄H₉-t | " | " | 128~132 |
| 410 | " | " | " | " | NHC₃H₇ | " | " | 57~60 |
| 411 | " | " | " | " | NHC₃H₇-i | " | " | 69~73 |
| 412 | " | " | " | " | Cl | OC₂H₅ | CH | 73~78 |
| 413 | " | " | " | " | N(CH₃)₂ | " | " | 101~105 |
| 414 | 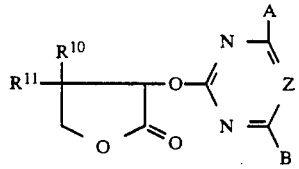 | H.H₂NC₃H₇-i | S | OCH₃ | OCH₃ | " | 68~73 |

TABLE 2

$$R^{11}-\underset{\underset{O}{\diagdown}}{\overset{R^{10}}{\diagup}}\underset{\underset{O}{\diagdown}}{\overset{}{\diagup}}\underset{O}{\overset{}{\diagdown}}-\underset{\underset{B}{\overset{N=}{\diagdown}}}{\overset{N=A}{\diagup}}Z$$

| Compound No. | $R^{10}$ | $R^{11}$ | A | B | Z | Melting point (°C.) or refractive index ($n_D^{20}$) |
|---|---|---|---|---|---|---|
| 415 | H | H | OCH₃ | OCH₃ | CH | 1.5210 |
| 416 | CH₃ | CH₃ | " | " | " | 165~170 |
| 417 | " | " | " | " | " | 139~142 |
| 418 | " | " | " | " | N | 104~106 |
| 419 | " | " | CH₃ | CH₃ | CH | 118~122 |

Compound 416 is a S(+) form.

Among the compounds of the present invention, Compound Nos. 4, 9, 65, 42, 66, 132, 133, 315, 153, 331, 326 and 336 are particularly excellent as herbicides.

The compounds of the present invention can be prepared by the processes of the following reaction schemes (1) to (6). However, the present invention is by no means restricted by such specific processes.

(1)

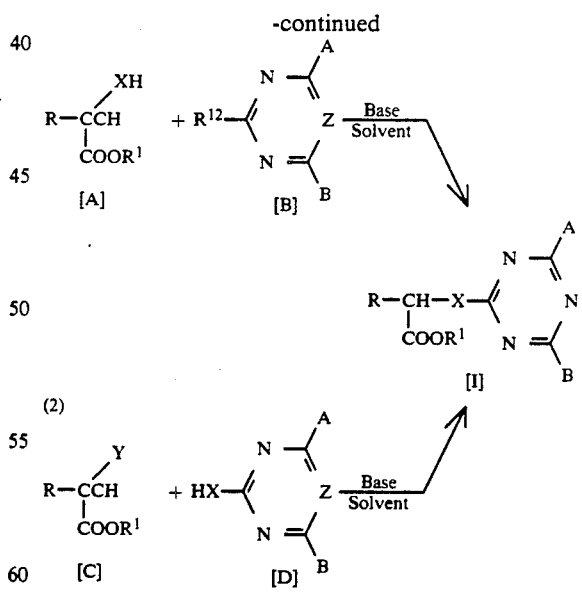

In the above formulas, $R^{12}$ is a halogen atom, an alkylsulfonyl group, a benzylsulfonyl group or a substituted benzylsulfonyl group, Y is a halogen atom or a methylsulfonyloxy group, and R, $R^1$, A, B, X and Z are as defined above.

The compound of the formula I can be prepared by reacting the compound of the formula A with the compound of the formula B as shown in reaction scheme (1), or by reacting the compound of the formula C with the compound of the formula D as shown in reaction scheme (2) in the presence of at least one equivalent of a base in a solvent at a temperature within a range of from room temperature to the boiling point of the solvent for from 0.5 to 24 hours. As the base, an alkali metal such as sodium metal or potassium metal, and an alkali metal hydride or alkaline earth metal hydride such as sodium hydride, potassium hydride or calcium hydride, an alkali metal carbonate such as sodium carbonate or potassium carbonate, an alkali metal hydroxide such as sodium hydroxide or potassium hydroxide or an organic amine such as triethylamine or pyridine, may be employed.

As the solvent, a hydrocarbon solvent such as benzene, toluene or xylene, a halogenated hydrocarbon solvent such as methylene chloride or chloroform, an alcohol solvent such as metanol, ethanol or 2-propanol, an ether solvent such as ethyl ether, tetrahydrofuran or dioxane, a ketone solvent such as acetone or methyl ethyl ketone, an ester solvent such as methyl acetate or ethyl acetate, an aprotic polar solvent such as N,N-dimethylformamide, N,N-dimethylacetamide or dimethylsulfoxide, acetonitrile or water, may be used.

A compound of the formula I of the present invention wherein $R^1$ is a hydrogen atom, can be prepared by the reaction in accordance with reaction scheme (1) or (2) using at least two equivalents of a base, followed by acidification.

by reacting the compound of the formula E with the compound of the formula B in the presence of a base in a suitable solvent at a temprature range of from $-10°$ C. to the boiling point of the solvent for from 0.5 to 24 hours to obtain the compound of the formula F, and oxdizing the compound of the formula F by an oxidizing agent in the presence of a solvent.

As the base to be used in the preparation of the compound of the formula F, an alkali metal amide such as lithium diisopropylamide, an alkali metal such as sodium metal or potassium metal, an alkali metal hydride or alkaline earth metal hydride such as sodium hydride, potassium hydride or calcium hydride, an alkali metal carbonate such as sodium carbonate or potassium carbonate, an alkali metal hydroxide such as sodium hydroxide or potassium hydroxide or an organic amine such as triethylamine or pyridine, may be employed. However, if such a base is present in the step for preparation of the compound of the formula E, it is unnecessary to further add such a base. As the solvent, a hydrocarbon solvent such as benzene, toluene or xylene, a halogenated hydrocarbon solvent such as methylene chloride or chloroform, an alcohol solvent such as methanol, ethanol or 2-propanol, an ether solvent such as ethyl ether, tetrahydrofuran or dioxane, a ketone solvent such as acetone or methyl ethyl ketone, an ester solvent such as methyl acetate or ethyl acetate, an aprotic polar solvent such as N,N-dimethylformamide, N,N-dimethylacetamide or dimethylsulfoxide, acetonitrile or water, may be used.

As the oxidizing agent oxidizing the compound of the formula F to be used in the preparation of the compound of the formula II of the present invention, a permanganate, silver oxide or a permanganate-periodic acid, may be mentioned.

As the solvent to be used in the oxidation, water, acetic acid or a solvent mixture such as water-acetone or water-acetic acid, may be mentioned. The reaction may be conducted at a temperature within a range of from room temperature to the boiling point of the solvent for from 1 to 24 hours.

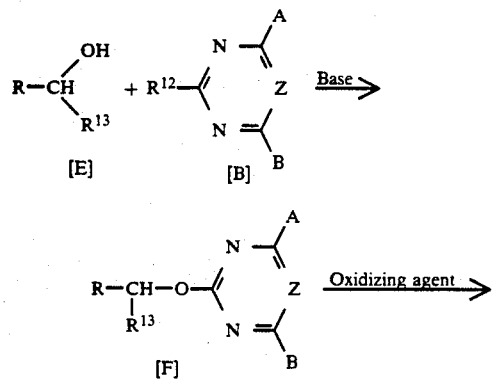

(3)

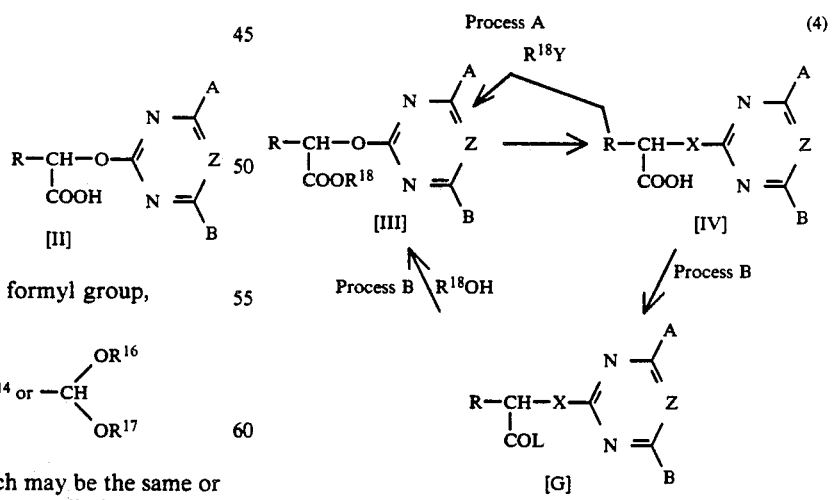

(4)

In the above formulas, $R^{13}$ is a formyl group,

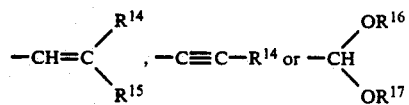

wherein each of $R^{14}$ and $R^{15}$ which may be the same or different is a hydrogen atom or a lower alkyl group, and each of $R^{16}$ and $R^{17}$ which may be the same or different is a lower alkyl group, and R, $R^{12}$, A, B and Z are as defined above.

The compound of the formula II of the present invention as shown in reaction scheme (3), can be prepared In the above formulas, $R^{18}$ is an alkyl group, an alkenyl group, an alkynyl group or a benzyl group which may be substituted by a halogen atom or an alkoxy group, L is a halogen atom, an imidazolyl group or $-OCOR^{19}$ wherein $R^{19}$ is a lower alkyl group or a phenyl group, and R, A, B, X, Y and Z are as defined above.

The compound of the formula IV of the present invention as shown in reaction scheme (4) can be prepared by hydrolyzing the compound of the formula III in the presence of at least one equivalent of a base in water at a temperature with a range of from room temperature to the boiling point of the solvent for from 1 to 48 hours and bringing the reaction solution to be neutral or acidic with an acid. As the base, an alkali metal hydroxide such as sodium hydroxide or potassium hydroxide may be employed. Further, in order to facilitate the reaction, an alcohol such as methanol or ethanol or a water-soluble organic solvent such as dioxane or acetonitrile, may be added to the reaction system.

The compound of the formula III of the present invention as shown in reaction scheme (4) can be prepared by esterifying the compound of the formula IV. Here, two processes will be described. However, it should be understood that the present invention is by no means restricted to these processes.

PROCESS A

The compound of the formula III can be prepared by reacting the compound of the formula IV with $R^{18}Y$ wherein $R^{18}$ and Y are as defined above, in the presence of a base in a suitable solvent at a temperature within a range of from room temperature to the boiling point of the solvent for 1 to 24 hours. As the base, an alkali metal carbonate such as sodium carbonate, potassium carbonate, sodium hydrogencarbonate or potassium hydrogencarbonate, an alkali metal hydride such as sodium hydride, potassium hydride or an organic amine such as triethylamine, pyridine or DBU, may be used. As the solvent, a hydrocarbon solvent such as benzene, toluene or xylene, an ether solvent such as ethyl ether, ethylene glycol dimethyl ether, tetrahydrofuran or dioxane or an aprotic polar solvent such as N,N-dimethylformamide, N,N-dimethylacetamide, dimethylsulfoxide or acetonitrile, may be employed. Further, as a catalyst, crown ether, N,N,N',N'-tetramethylethylenediamine may be used.

PROCESS B

The compound of the formula IV is reacted with a suitable reagent to prepare the compound of the formula G. Then, after isolating it or without isolating it, it is reacted with $R^{18}OH$ wherein $R^{18}$ is as defined above to obtain the compound of the formula III. Here, as the reagent to be used in the preparation of the compound of the formula G, thionyl chloride, oxalic acid dichloride, a chlorocarbonate or carbonyldiimidazole may be mentioned. As the solvent, a hydrocarbon solvent such as benzene, toluene or xylene, a halogenated hydrocarbon solvent such as methylene chloride or chloroform, an ether solvent such as diethyl ether, ethyleneglycol dimethyl ether or tetrahydrofuran or an aprotic polar solvent such as N,N-dimethylformamide or acetonitrile may be used. The compound of the formula III can be prepared by the reaction of $R^{18}OH$ at a temperature within a range of from 0° C. to the boiling point of the solvent for 0.5 to 24 hours.

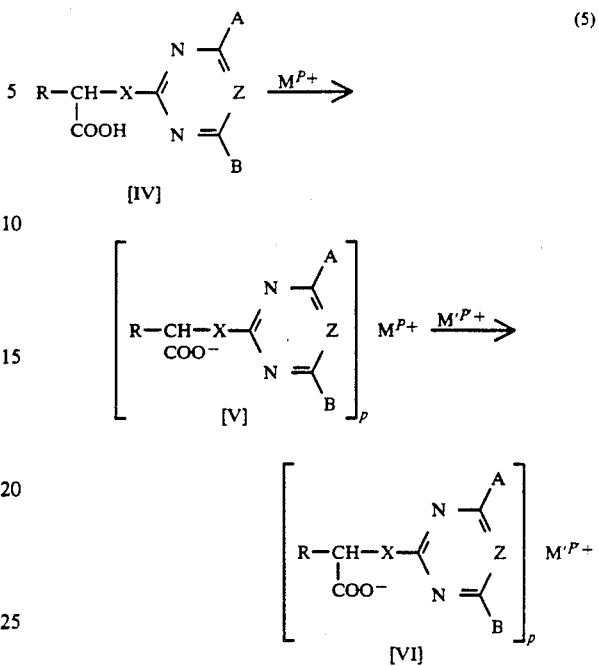

In the above formulas, each of $M^{P+}$ and $M'^{P+}$ is a cation such as an alkali metal, an alkaline earth metal or a transition metal, organic or inorganic ammonium, and each of P and P' is an electrical charge number of from 1 to 3.

The compound of the formula V as shown in reaction scheme (5) can be prepared by reacting the compound of the formula IV with a base in a solvent at a temperature within a range of from room temperature to the boiling point of the solvent for 5 minutes to 10 hours. As the solvent, a hydrocarbon solvent such as benzene, toluene or xylene, a halogenated hydrocarbon solvent such as methylene chloride or chloroform, an alcohol solvent such as methanol or ethanol, an ether solvent such as ethyl ether, ethyleneglygol dimethyl ether, tetrahydrofuran or dioxane, a ketone solvent such as acetone or methyl ethyl ketone, an ester solvent such as methyl acetate or ethyl acetate, acetonitrile, or water, may be mentioned. As the base, an alkali metal such as sodium metal or potassium metal, an alkali metal hydride or alkaline earth metal hydride such as sodium hydride, potassium hydride or calcium hydride, a carbonate such as sodium carbonate, potassium carbonate or calcium carbonate, an alkali metal hydroxide such as sodium hydroxide or potassium hydroxide, or a primary, secondary or tertiary organic amine, will be employed. Further, the compound of the formula VI can be prepared by subjecting the compound of the formula V to cation exchange in the above-mentioned solvent at a temperature within a range of from room temperature to the boiling point of the solvent for from 5 minutes to 10 hours.

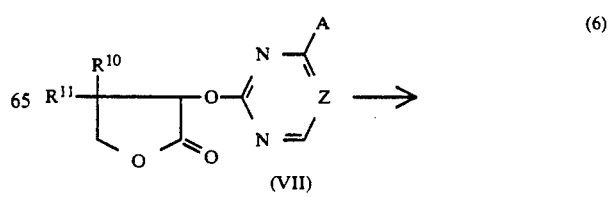

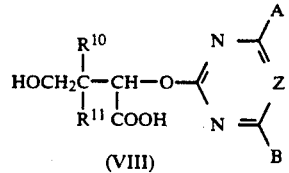

In the above formulas, each of $R^{10}$ and $R^{11}$ is a hydrogen atom or an alkyl group, and A, B and Z are as defined above.

The compound of the formula VIII as shown in reaction scheme (6) can be prepared by hydrolyzing the compound of the formula VII in the persence of at least one equivalent of a base and then bringing the reaction solution to be neutral or acidic with an acid.

As the base, an alkali metal hydroxide such as sodium hydroxide or potassium hydroxide may be employed. Further, in order to facilitate the reaction, the aforementioned water-soluble organic solvent may be added to the reaction system.

Now, the process for producing the intermediates to be used in the present invention will be mentioned as Reference Examples.

The compound of the formula A wherein X is an oxygen atom can be obtained by a usual method. For instance, an oxirane is prepared from the corresponding ketone by Darzens reaction, and then an aldehyde is prepared in accordance with the method disclosed in Org. Syn. III, 733 (1955). Then, the aldehyde is converted to a cyanohydrin, followed by hydrolysis to obtain such a compound. Further, specific processes for producing the compound of the formula A wherein X is a sulfur atom will be given in Reference Examples 1 and 2.

The compound of the formula C can be obtained by halogenating the α-position of a fatty acid in accordance with the method disclosed in Org. Syn. III, 848 (1955).

A specific process for producing the compound of the formula E wherein R is

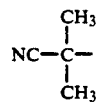

and $R^{13}$ is CH=CH—$CH_3$ will be described in Example 11.

REFERENCE EXAMPLE 1

Preparation of 3-phenyl-3-methyl-2-mercaptobutyric acid 15.2 g of diisopropylamine was added to 500 ml of dry tetrahydrofuran, and 84 g of a n-butyl lithium-hexane solution (15%) was dropwise added thereto at a temperature of from −30° to −40° C. under stirring. After completion of the dropwise addition, the mixture was stirred for further 30 minutes, and then the temperature was raised to 0° C. The reaction solution was stirred at 0° C. for 30 minutes and then cooled to −30° to −40° C. again. 17.8 g of 3-phenyl-3-methylbutyric acid dissolved in 50 ml of tetrahydrofuran and 11.6 ml of hexamethylphosphoric acid triamide were dropwise added thereto. The mixture was stirred for one hour and further stirred at 0° C. for one hour. Then, the reaction solution was cooled to −10° C., and 3.2 g of sulfur powder was added thereto. The temperature was gradually raised to room temperature and stirred overnight. Water was added to the reaction solution, and the reaction soltuion was acidified with citric acid. The organic layer was dried over anhydrous sodium sulfate and concentrated to obtain a brown solid. The solid and 7 g of activated zinc powder were added to 70 ml of acetic acid and refluxed for 6 hours. The reaction solution was poured into water, and a precipitated zinc complex was collected by filtration. This complex was stirred in a 48% sodium hydroxide aqueous solution at 90° C. for 30 minutes. The reaction solution was poured into water and subjected to filtration. Then, the filtrate was acidified with hydrochloric acid and extracted with chloroform. The organic layer was washed with water, dried over anhydrous sodium sulfate and concentrated to obtain 9.6 g of 3-phenyl-3-methyl-2-mercaptobutyric acid.

Melting point: 70°–73° C.

REFERENCE EXAMPLE 2

Preparation of 3,3-dimethyl-2-mercaptobutyric acid 9.2 g of 3,3-dimethyl-2-mercarptobutyric acid was obtained in the same manner as in Reference Example 1 except that 3,3-dimethyl-2-mercaptobutyric acid was used instead of 3-phenyl-3-methylbutyric acid.

Melting point: 80°–81° C.

Now, the present invention will be described in further detail with reference to Examples. However, it should be understood that the present invention is by no means restricted to such specific Examples.

EXAMPLE 1

Preparation of ethyl 2-(4,6-dimethoxypyrimidin-2-yl)oxy-3-methyl-3-phenylbutyrate (Compound No. 44)

4.5 g of ethyl 2-hydroxy-3-methyl-3-phenylbutyric acid, 4.6 g of 4,6-dimethoxy-2-methylsulfonylpyrimidine, 5,3 g of anhydrous potassium carbonate and 50 ml of N,N-dimethylformamide were introduced to a round bottom flask, and the mixture was stirred at 100° C. for 3 hours. Then, the reaction mixture was poured into ice water and extracted twice with 50 ml of ethyl acetate. The extract was washed with water and then dried over anhydrous sodium sulfate overnight. An inorganic salt was removed by filtration, and then the solvent was distilled off under reduced pressure to obtain 7 g of crude crystals. The crude crystals were recrystallized from ethanol to obtain 5.6 g of the desired product.

Melting point: 123°–124° C.

EXAMPLE 2

Preparation of 2-(4,6-dimethoxypyrimidin-2-yl)oxy-3-methyl-3-phenylbutyric acid (Compound No. 42)

4.8 g of ethyl 2-(4,6-dimethoxypyrimidin-2-yl)oxy 3-methyl-3-phenylbutyrate, 11 ml of a 10% sodium hydroxide aqueous solution and 50 ml of ethanol were introduced to a round bottom flask and reacted for 2 hours under refluxing. Then, a large portion of ethanol was distilled off under reduced pressure. 50 ml of water was added to the residue thereby obtained, and neutral organic substances were removed by extraction with chloroform. Then, the solution was adjusted to pH 3 to 4 with 5% hydrochloric acid, and extracted twice with 50 ml of ethyl acetate. The extract was washed with water and then dried over anhydrous sodium sulfate overnight. An inorganic salt was removed by filtration, and then, the solvent was distilled off under reduced pressure to obtain 4.0 g of crude crystals. The crude crystals were recrystallized from ethanol to obtain 2.8 g of the desired product.

Melting point: 163°-165 ° C.

EXAMPLE 3

Preparation of sodium 3-(3-chlorophenyl)-2-(4,6-dimethoxypyrimidin-2-yl)oxy-3-methylbutyrate (Compound No. 61)

1 g of 3-(3-chlorophenyl)-2-(4,6-dimethoxypyrimidin-2-yl)oxy-3-methylbutyric acid was dissolved in 10 ml of acetone, and 0.6 g of 28% sodium methoxide was added thereto. The mixture was stirred at room temperature for one hour, and then the precipitated crystals collected by filtration to obtain 0.9 g of the desired product.

Melting point: 220°-226° C.

EXAMPLE 4

Preparation of proparqyl 2-(4,6-dimethoxypyrimidin-2-yl)oxy-3-methyl-3-(3-methylphenyl)butyrate (Compound No. 101)

1.1 g of 2-(4,6-dimethoxypymidin-2-yl)oxy-3-methyl-3-(3-methylphenyl)butyric acid, 0.5 g of anhydrous potassium carbonate, 0.5 g of propargyl bromide and 20 ml of N,N-dimethylformamide were introduced to a round bottom flask and stirred at 80° C. for 4 hours. Then, the reaction mixture was poured into ice water and extracted twice with 50 ml of toluene. The extract was washed with water and then dried over anhydrous sodium sulfate overnight. An inorganic salt was removed by filtration, and then the solvent was distilled off under reduced pressure to obtain 1.2 g of a viscous liquid. The viscous liquid was dissolved in N-hexane, and the solution was left to stand at room temperature to precipitate crystals. The crystals were collected by filtration to obtain 0.9 g of the desired product.

Melting point: 95°-97° C.

EXAMPLE 5

Preparation of methyl 2-(4,6-dimethoxy-S-triazin-2-yl)oxy-3-methyl-3-phenyl)butyrate (Compound No. 151)

2.1 g of methyl 2-hydroxy-3-methyl-3-phenylbutyrate, 1.8 g of 2-chloro-4,6-dimethoxy-S-triazine and 1.7 g of potassium carbonate were added to 50 ml of acetonitrile, and the mixture was refluxed for 20 hours. The reaction solution was cooled, then poured into water and extracted with 100 ml of ethyl acetate. The organic layer was washed twice with a sodium chloride aqueous solution, then dried over anhydrous sodium sulfate and concentrated under reduced pressure. The liquid substance thereby obtained was purified by silica gel column chromatography (eluent: hexane/ethyl acetate=6/1) to obtain 1.2 g of the desired product.

Melting point: 85°-87° C.

EXAMPLE 6

Preparation of methyl 2-(4,6-dimethylpyrimidin-2-yl)oxy-3,3-dimethylbutyrate (Compound No. 13)

2.9 g of methyl 2-hydroxy-3,3-dimethybutyrate, 4,1 g of 4.6-dimethyl-2-methylsulfonylpyrimidine and 3.3 g of potassium carbonate were added to 50 ml of N,N-dimethylformamide, and the mixture was stirred at 100° C. for 4 hours. The reaction solution was cooled to room temperature, poured into water and extracted with 100 ml of ethyl acetate. The organic layer was washed twice with a sodium chloride aqueous solution, dried over anhydrous sodium sulfate and concentrated under reduced pressure. The liquid substance thereby obtained was purified by silica gel column chromatography (eluent: hexane/ethyl acetate=6/1) to obtain 4.2 g of the desired product.

Refractive index $n_D^{20}$: 1.4868

EXAMPLE 7

Preparation of 2-(4,6-dimethylpyrimidin-2-yl)oxy-3,3-dimethylbutyric acid (Compound No.12)

1.5 g of methyl 2-(4,6-dimethylpyrimidin-2-yl)oxy-3,3-dimethylbutyrate was dissolved in 10 ml of methanol, and 10 ml of an aqueous solution containing 0.5 g of potassium hydroxide was added thereto. The mixture was stirred at room temperature for 12 hours and then shaked with 210 ml of toluene and 30 ml of water in a separatory funnel. The aqueous layer was acidified with an oxalic acid aqueous solution and extracted with 100 ml of ethyl ) ether. The organic layer was dried over anhydrous sodium sulfate and concentrated under reduced pressure to obtain 1.2 g of the desired product.

Melting point: 167°-169° C.

EXAMPLE 8

Preparation of 2 (4,6-dimethoxypyrimidin-2-yl)oxy-3,3-dimethyl-γ-butyrolactone (Compound No. 247)

13.0 g of 2-hydroxy 3,3-dimethyl-γ-butyrolactone and 24.0 g of 4,6-dimethoxy-2-methylsulfonylpyrimidine were mixed in 80 ml of N,N-dimethylformamide in the presence of 27.6 g of potassium carbonate at a temperature of from 90° to 100° C. for 3 hours. The reaction solution was cooled to room temperature, then, poured into ice water and extracted with ethyl ether. The extract was washed twice with water and dried over anhydrous magnesium sulfate. The desiccating agent was removed by filtration and then the filtrate was concentrated to obtain 26.0 g of the desired product.

Melting point: 139°-142° C.

EXAMPLE 9

Preparation of 2-(4,6-dimethoxypyrimidin-2-yl)oxy-4-hydroxy-3,3-dimethylbutyric acid (Compound No. 77)

To 150 ml of an ethanol solution of 5.4 g of 2-(4,6-dimethoxypyrimidin-2-yl)oxy-3,3-dimethyl-γ- butyrolactone, 20 ml of an aqueous solution of 1.2 g of sodium hydroxide was added, and then, the mixture was stirred at room temperature for one hour. Ethanol was evaporated under reduced pressure, and the reaction solution was adjusted to pH 2 to 3 with 5% hydrochloric acid. The reaction solution was extracted twice with ethyl acetate, washed twice with a sodium chloride aqueous solution and then dried over anhydrous magnesium sulfate. The desiccating agent was removed by filtration, and then, the filtrate was concentrated under reduced pressure to obtain 4.7 g of the desired product.

Melting point: 104°-110° C.

EXAMPLE 10

Preparation of methyl 2-(4,6-dimethoxypyrimidin-2-yl)oxyhexanoate (Compound No. 8)

3.5 g of 2-hydroxy-4,6-dimethoxypyrimidine, 4.7 g of methyl 2-bromohexanoate, 50 ml of N,N-dimethylformamide and 3.3 g of anhydrous potassium carbonate were stirred at a temperature of from 85° to 90° C. for 3 hours. The reaction mixture was cooled to room temperature and then diluted with water. This aqueous mixture was extracted with ethyl ether. The ethyl ether extract was washed with water and dried. Then, ethyl ether was removed by distillation under reduced pressure to obtain a slightly yellow oily substance. The slightly yellow oily substance was purified by silica gel column chromatography (eluent: hexane/ethyl acetate=6/1) to obtain 4.7 g of the desired product.

Refractive index $n_D^{20}$: 1.4868

EXAMPLE 11

Preparation of 3-cyano-2-(4,6-dimethoxypyrimidin-2-yl)oxy-3-methylbutyric acid (Compound No. 155)

To a tetrahydrofuran solution of lithium diisopropylamide prepared from 3.3 g of diisopropylamine and 14.1 g of a 15% n-butyl lithium hexane solution dissolved in 50 ml of tetrahydrofuran at −20° C., 2.3 g of isobutyronitrile and 2.1 g of crotonaldehyde were added in turn at −10° C. to obtain 5-cyano-4 hydroxy-5-methyl-2-hexane. To this reaction solution, 6.5 g of 4,6-dimethoxy-2-methylsulfonylpyrimidine was added, and the mixture was stirred overnight. The reaction solution was neutralized with a 10% hydrochloric acid aqueous solution, extracted with ethyl acetate, washed with water and dried. The solvent was distilled off to obtain crystals of 5-cyano-4-(4,6-dimethoxypyrimidin-2-yl)oxy-5-methyl-2-hexene (melting point: 91°-92° C.). The crystals thereby obtained were dissolved in 100 ml of acetone, and an aqueous solution of 1.7 g of potassium permanganate were added thereto at room temperature. The mixture was stirred for one hour. Acetone was distilled off and then the reaction solution was extracted with ethyl acetate. The ethyl acetate layer was washed and adjusted to pH 4 to obtain 0.68 g of the desired product.

Melting point: 142°-150° C.

EXAMPLE 12

Preparation of ethyl 2-(4,6-dimethoxypyrimidin-2-yl)thiocyclopentyl acetate (Compound No. 132)

4.0 g of 2-mercapto-4,6-dimethoxypyrimidine, 4.8 g of ethyl 2-bromocyclopentyl acetate, 50 ml of N,N-dimethylformamide and 3.4 g of anhydrous potassium carbonate were stirred at 90° C. for 3 hours. The reaction mixture was cooled to room temperature and then diluted with water. The aqueous mixture was extracted with ethyl ether. The ethyl ether extract was washed with water and dried. Then, ethyl ether was removed by distillation under reduced pressure to obtain an yellow oily substance. The yellow oily substance was purified by silica gel column chromatography (eluent: hexane/ethyl acetate=6/1) to obtain 3.6 g of the desired product.

Refractive index $n_D^{20}$: 1.5310

EXAMPLE 13

Preparation of 2-(4,6-dimethoxypyrimidin-2-yl)thiocyclopentyl acetic acid (Compound No. 133)

To a mixture solution of 20 ml of ethanol, 20 ml of water and 0.4 g of sodium hydroxide, 2.5 g of ethyl 2-(4,6-dimethoxypyrimidin-2-yl)thiocyclopentyl acetate was added, and the mixture was stirred at a temperature of from 45° to 50° C. for 3 hours. Ethanol was removed by distillation under reduced pressure, and the residue was extracted with toluene. The toluene layer was removed. The aqueous layer was adjusted to pH 2 to 3 with a 5% hydrochloric acid aqueous solution and extracted with ethyl ether. The ethyl ether extract was washed with water and dried. Then, ethyl ether was removed by distillaton under reduced pressure to obtain a white solid. The solid was recrystallized from isopropyl ether to obtain 1.6 g of the desired product.

Melting point: 125°-127° C.

EXAMPLE 14

Preparation of ferric 2-(4,6-dimethoxypyrimidin-2-yl)oxy-3,3-dimethylbutyrate (Compound No. 244)

To 5 ml of an aqueous solution of 0.2 g of sodium hydroxide, 1.0 g of 2-(4,6-dimethoxypyrimidin-2-yl)oxy-3,3-dimethylbutyric acid was dissolved to prepare a sodium salt. 5 ml of aqueous solution of 1.1 g of ferric trichloride (hexahydrate) was added thereto. Precipitated salts were collected by filtration, thoroughly washed with water and dried to obtain 1.1 g of the desired product.

Melting point: 178°-181° C.

EXAMPLE 15

Preparation of ethyl 2-(4,6-dimethoxypyrimidin-2-yl)oxy(1,2-epoxycyclohexyl)acetate (Compound No. 245)

To a suspension of 5.9 g of methachloro perbenzoic acid in 70 ml of methylene chloride, 7.4 g of ethyl 2-

(4,6-dimethoxypyrimidin-2-yl)oxy-2-(1-cyclohexenyl-)acetate was added at a temperature of from 5° to 10° C. over a period of 30 minutes. The reaction mixture was stirred at room temperature for 12 hours, and formed crystals were removed by filtration. Then, the filtrate was washed a few times with a diluted sodium carbonate aqueous solution and water and dried over anhydrous sodium sulfate. Then, methylene chloride was removed by distillation under reduced pressure to obtain a yellow residue. The residue was purified by silica gel column chromatography (eluent: hexane/ethyl acetate=6/1) to obtain 1.9 g of the desired product.

Melting point: 108°–110° C.

EXAMPLE 16

Preparation of ethyl 2-(4,6-dimethoxypyrimidin-2-yl)thio-2-(2,4-dimethylcyclopentyl)acetate (Compound No. 279)

3.2 g of 2-mercapto-4,6-dimethoxypyrimidine, 4.9 g of ethyl 2-bromo-2-(2,4-dimethylcyclopentyl)acetate, 50 ml of N,N-dimethylformamide and 2.7 g of anhydrous potassium carbonate were stirred at a temperature of from 85° to 90° C. for 3 hours. The reaction mixture was cooled to room temperature and then diluted with water. The aqueous mixture was extracted with ethyl ether. The ethyl ether extract was washed with water and dried. Then, ethyl ether was removed by distillation under reduced pressure to obtain a slightly yellow oily substance. The slightly yellow oily substance was purfied by silica gel column chromatography (eluent: hexane/ethyl acetate=10/1) to obtain 4.5 g of the desired product.

Refractive index $n_D^{20}$: 1.5202

EXAMPLE 17

Preparation of 2-(4,6-dimethoxypyrimidin-2-yl)oxy-3-trifluoromethylbutyric acid (Compound No. 376)

To a mixture solution of 50 ml of methanol, 50 ml of water and 1.0 g of sodium hydroxide, 8.0 g of methyl 2-(4,6-dimethoxypyrimidin-2-yl)oxy-3-trifluoromethylbutyrate was added, and the mixture was stirred at a temperature of from 45° to 50° C. for 4 hours. Methanol was removed by distillation under reduced pressure, and the residue was extracted with toluene. The toluene layer was removed, and the aqueous layer was adjusted to pH 2 to 3 with a 5% hydrochloric acid aqueous solution and extracted with ethyl ether. The ethyl ether extract was washed and dried. Then, ethyl ether was removed by distillation under reduced pressure to obtain a slightly yellow solid. The solid was recrystallized from n-hexane to obtain 5.9 g of the desired product.

Melting point: 112°–114° C.

EXAMPLE 18

Preparation of ethyl 2-(4,6-dimethoxypyrimidin-2-yl)thio-2-(1-cyclopentenyl)acetate (Compound No. 318)

10.4 g of 2-mercapto-4,6-dimethoxypyrimidine, 15.0 g of ethyl 2-(1-cyclopentenyl)-2-(methylsulfonyloxy)acetate, 100 ml of N,N-dimethylformamide and 9.2 g of anhydrous potassium carbonate were stirred at 90° C. for 5 hours. The reaction mixture was cooled to room temperature and then diluted with water. The aqueous mixture was extracted with ethyl ether. The ethyl ether extract was washed with water and dried. Then, ethyl ether was removed by distillation under reduced pressure to obtain an yellow oily substance. The yellow oily substance was purified by silica gel column chromatography (eluent: hexane/ethyl acetate=10/1) to obtain 9.7 g of the desired product.

Refractive index $n_D^{20}$: 1.5482

EXAMPLE 19

Preparation of 2-(4,6-dimethoxy-S-triazin-2-yl)thio-2-cyclopentyl acetic acid (Compound No. 343)

To a mixture solution of 6.0 g of 2-mercapto-2-cyclopentyl acetic acid, 4.2 g of potassium hydroxide and 50 ml of water, a solution of 30 ml of acetone and 6.6 g of 2-chloro-4,6 dimethoxy-S-triazine was added at a temperature of from 0° to 5° C. for 20 minutes. Then, the reaction mixture was stirred at room temperature for 1.5 hours. Acetone was removed by distillation under reduced pressure, and the residue was extracted with ethyl ether. The ethyl ether layer was removed, and the aqueous layer was adjsuted to pH 2 to 3 with a 5% hydrochloric acid aqueous solution and extracted with ethyl acetate. The ethyl acetate extract was washed with water and dried. Then, ethyl acetate was removed by distillation under reduced pressure to obtain a white solid. The solid was recrystallized from isopropyl ether and n-hexane to obtain 4.5 g of the desired product.

Melting point: 106°–110° C.

EXAMPLE 20

Preparation of isopropylammonium 2 (4,6-dimethoxypyrimidin-2-yl)thio-2 -cyclopentyl acetate (Compound No. 414)

A mixture of 5.0 g of 2-(4,6 dimethoxypyrimidin-2-yl)thio-2-cyclopentyl acetic acid, 1.0 g of isopropylamine and 80 ml of methanol was stirred at room temperature for 1.5 hours. Methanol was removed by distillation under reduced pressure. Isopropyl ether was added to the residue, and the mixture was stirred at room temperature for 0.5 hour. Formed crystals were collected by filtration, washed with n-hexane and then dried to obtain 4.3 g of the desired product.

Melting point: 68°–73° C.

EXAMPLE 21

Preparation of ethyl 2-(4,6-dimethoxypyrimidin 2-yl)oxy-3-(2,6-dichlorophenyl)propionate (Compound No. 257)

50 ml of a N,N-dimethylformamide solution of 1.65 g of 2-(4,6-dimethoxypyrimidin-2-yl)oxy-3-(2,6-dichlorophenyl)propionic acid, 0.5 g of ethyl bromide 0.6 g of potassium carbonate was stirred at 80° C. for 2 hours under heating. The reaction solution was poured into water and extracted with ethyl acetate. The ethyl acetate layer was washed and dried. Then, the solvent was distilled off to obtain colorless crystals.

Melting point: 130°–132° C.

EAMPLE 22

Preparation of 2-(1-indany)-2-(4,6-dimethoxypyrimidin-2-yl)oxy acetic acid (Compound No. 373)

A mixture solution of 3.8 g of methyl 2-(1-indanyl)-2-(4,6-dimethoxypyrimidin-2-yl)oxy acetate, 6.2 g of potassium hydroxide, 60 ml of water and 60 ml of ethanol was stirred at room temperature for 5 hours. The solvent was distilled off, and residue was extracted with ethyl acetate. The ethyl acetate layer was extracted with a sodium hydrogencarbonate aqueous solution. The aqueous layer was acidified and then extracted with ethyl acetate. The ethyl acetate layer was washed with water and dried. The solvent was distilled off to obtain 2.4 g of the desired product.

Melting point: 113°-117° C.

EXAMPLE 23

Preparation of methyl 2-(1-indanyl)-2-(4,6-dimethoxypyrimidin-2-yl)oxy acetate (Compound No. 374)

100 ml of a N,N-dimethylformamide solution of 8.1 g of methyl 2-(2-indanyl)-2-hydroxy acetate, 9.0 g of 4,6-dimethoxy-2-methylsulfonylpyrimidine and 6.0 g of potassium carbonate was reacted at 100° C. under heating for 5 hours. After completion of the reaction, the reaction solution was poured into water and extracted with ethyl acetate. The extract was washed with water and dried. Then, the solvent was distilled off under reduced pressure, and the residue thereby obtained was purified by silica gel column chromatography (eluent: hexane/ethyl acetate=6/1) to obtain 5.8 g of the desired product.

Melting: 93°-96° C.

EXAMPLE 24

Preparation of 2-(2-methylindan-1-yl) 2-(4,6-dimethoxypyrimidin-2-yl)oxy acetic acid (Compound No. 383)

50 ml of a N,N-dimethylformamide solution of 2.9 g of methyl 2-(2-methylindan-1-yl)-2-hydroxy acetate, 2.9 g of 4.6-dimethoxy-2-methylsulfonylpyrimidine and 2.1 g of potassium carbonate was reacted at 80° C. under heating for 3 hours. After completion of the reaction, the reaction solution was poured into water and extracted with ethyl ether. The extract was washed with water and dried. Then, the solvent was distilled off under reduced pressure to obtain 2.3 g of methyl 2-(2-methylindan-1-yl)-2-(4,6-dimethoxypyrimidin-2-yl)oxy acetate (melting point: 102°-104° C.).

A solution mixture of 3.2 g of methyl 2-(2-methylindan-1-yl)-2-(4,6-dimethoxypyrimidin-2-yl)oxy acetate, 1.0 g of potassium hydroxide, 100 ml of water and 100 ml actone was reacted at 60° C. for 3 hours. The solvent was distilled off, and the residue was extracted with ethyl ether. The ethyl ether layer was extracted with a sodium hydrogencarbonate aqueous solution and the aqueous layer was acidified and extracted with ethyl ether. The ethyl ether layer was washed with water and dried. The solvent was distilled off to obtain 1.9 g of the desired product.

Melting point: 148°-151° C.

EXAMPLE 25

Preparation of 3,3-dimethyl-2-(4,6-dimethoxy-S-triazin-2-yl)oxybutyric acid (Compound No. 336)

4.8 g of benzyl 3,3-dimethyl-2-hydroxyacetate and 3.4 g of 2-chloro-4,6-dimethoxy-S-triazine were dissolved in 100 ml of tetrahydrofuran, and the solution was stirred under cooling with ice. 1.2 g (60%) of sodium hydride was added thereto. The temperature was raised to room temperature, and the mixture was stirred overnight. The reaction solution was poured into water and extracted with 80 ml of ethyl acetate. The organic layer was washed with water, dried over anhydrous sodium sulfate and concentrated to obtain an oily substance. The oily substance was purified by silica gel column chromatography (eluent: hexane/ethyl acetate=10/1) to obtain 6.2 g of benzyl 3,3-dimethyl-2-(4,6-dimethoxy-S-triazin-2-yl)oxybutyrate (Compound No. 337, melting point: 63°-66° C.).

4.5 g of benzyl 3,3-dimethyl-2-(4,6-dimethoxy-S-triazin-2-yl)oxybutyrate and 0.5 g (10%) of palladium carbon wetted with 2 ml of acetic acid were added to 100 ml of ethanol. 257 ml of hydrogen was added thereto at room temperature under stirring. The reaction solution was subjected to filtration, and the filtrate was extracted twice with 200 ml of ethyl acetate. The organic layer was dried over anhydrous sodium sulfate and concentrated under reduced pressure to obtain 3.1 g of the desired product.

Melting point: 37°-40° C.

EXAMPLE 26

Preparation of 3-phenyl-3-methyl-2-(4,6-dimethoxy-S-triazin-2-ylthio)-butyric acid (Compound No. 340)

1.9 g of 3-phenyl-3-methyl-2-mercaptobutyric acid was dissolved in 50 ml of acetone, and 1.2 g of potassium hydroxide dissolved in 5 ml of water was added thereto under cooling with ice. 1.5 g of 2-chloro-4,6-dimethoxy-S-triazine dissolved in 20 ml of acetone was added thereto. The mixture was stirred for 30 minutes. Then, the reaction solution was poured into water and extracted with 50 ml of ethyl acetate. The aqueous layer was acidified with a citric acid aqueous solution and extracted with 100 ml of chloroform. The organic layer was washed with water, dried over anhydrous sodium sulfate and concentrated to obtain 2.2 g of the desired product.

Melting point: 115°-118° C.

EXAMPLE 27

Preparation of ethyl 2-(4,6-dimethoxypyrimidin-2-yl)oxy-2-(1,2,3,4-tetrahydronaphthalen-1-oxo-2-yl)acetate (Compound No. 379)

3.0 g of ethyl 2-hydroxy-2-(1,2,3,4-tetrahydronaphthalen-1-oxo-2-yl)acetate and 2.6 g of 4,6-dimethoxy-2-methylsulfonylpyrimidine were dissolved in 50 ml of tetrahydrofuran, and 0.8 g (60%) of sodium hydride was added thereto at 5° C. The mixture was stirred overnight. Then, the reaction solution was poured into water and extracted with ethyl acetate. The ethyl acetate extract was dried over anhydrous sodium sulfate and concentrated. The residue thereby obtained was purified by silica gel colum chromatography (eluent: hexane/ethyl acetate=6/1) to obtain 0.4 g of the desired product.

The herbicidal composition of the present invention comprises a herbicidally effective amount of the compound of the present invention and an agricultural adjuvant. The herbicide of the present invention may be used as it is or may be formulated in various formulations such as a wettable powder, a granule, an emulsifiable concentrate, a flowable, a dry flowable, a liquid formulation, or a dust by blending it in an amount of from 0.5 to 95 parts by weight, preferably from 1 to 80 parts by weight, with a carrier, a surfactant, a dispersing agent or an adjuvant which is commonly employed for the formulation of agricultural chemicals, in an amount to make up the total of 100 parts by weight.

As the carrier to be used for the formulation, there may be mentioned a solid carrier such as jeeklite, talc, bentonite, clay, kaolin, diatomaceous earth, white carbon, vermiculite, slaked lime, silica sand, ammonium sulfate or urea, or a liquid carrier such as isopropyl alcohol, xylene, cyclohexane or methyl naphthalene. As the surfactant and dispersing agent, there may be mentioned, for example, an alcohol-sulfuric acid ester, an alkyl aryl sulfonate, lignin sulfonate, a polyoxyethylene glycol ether, a polyoxyethylene alkyl aryl ether or a polyoxyethylene sorbitol mono-alkylate. As the adjuvant, for example, carboxymethyl cellulose, polyethylene glycol or gum arabic may be mentioned.

The proportion of the compound of the present invention in the formulation may vary depending upon the type of the formulation, the application method, the application site, timing, etc. Therefore, it can not generally be defined. However, it is usually from 5 to 90% by weight in a wettable powder, from 5 to 80% by weight in an emulsifiable concentrate, from 1 to 60% by weight in a flowable, from 0.5 to 20% by weight in a granule, from 5 to 80% by weight in a liquid formulation, from 0.5 to 10% by weight in a dust and from 5 to 90% by weight in a dry flowable.

In practical use, such a herbicide may be diluted to a suitable concentration before application, or may directly be applied. Further, the herbicide of the present invention can be used in combination with other herbicides.

Now, Formulation Examples for the herbicidal composition of the present invention will be given. However, it should be understood that the present invention is by no means restricted to these specific Examples. In these Examples, "%" means "% by weight".

FORMULATION EXAMPLE 1

(wettable powder)

10% of Compound No. 1, 0.5% of Emulgen 810 (trademark, Kao Corporation), 0.5% of Demol N (trademark, Kao Corporation), 20% of Kunilite 201 (trademark, Kunimine Kogyo K.K.) and 69% of Jeeklite CA (trademark, Jeeklite Company Ltd.) were uniformly mixed and pulverized to obtain a wettable powder.

FORMULATION EXAMPLE 2

(emulsifiable concentrate)

30% of Compound No. 1, 20% of cyclohexanone, 11% of polyoxyethylene alkyl aryl ether, 4% of calcium alkylbenzenesulfonate and 35% of methyl naphthalene, were uniformly dissolved to obtain an emulsifiable concentrate.

FORMULATION EXAMPLE 3

(granule)

5% of Compound No. 1, 2% of a sodium salt of a lauryl alcohol-sulfuric acid ester, 5% of sodium lignin sulfonate, 2% of carboxymethyl cellulose and 86% of clay were uniformly mixed and pulverized. To 100 parts by weight of this mixture, 20 parts by weight of water was added, and the mixture was kneaded, and granulated into granules of from 14 to 32 mesh by means of an extrusion granulating machine, followed by drying to obtain granules.

FORMULATION EXAMPLE 4

(dust)

2% of Compound No. 1, 5% of diatomaceous earth and 93% of clay were uniformly mixed and pulverized to obtain a dust.

The herbicide of the present invention is capable of controlling various weeds in an upland field by soil treatment before or after the emergence of weeds or by foliage treatment. Further, the herbicide is capable of controlling various weeds in a paddy field by irrigated soil treatment before or after the emergence of weeds or by foliage treatment.

For soil treatment, the herbicide of the present invention is applied in a dose of from 0..1 g to 1 kg, preferably from 1 to 400 g of the active ingredient per 10 ares. For foliage treatment, it is diluted to a concentration of from 1 to 10,000 ppm for application.

The compounds and the herbicidal compositions of the present invention are capable of effectively controlling annual weeds such as barnyardgrass (*Echinochloa crusgalli*), crabgrass (*Digitaria sanguinalis*), goosegrass (*Eleusine indica*), green foxtail (*Setaria viridis*), giant foxtail (*Setaria faberi*), yellow foxtail (*Setaria glauca*), shattercane (*Sorghum bicolor*), proso millet (*Panicum miliaceum*), fall panicum (*Panicum dichotomiflorum*), itchgrass (*Rottoboelia exaltata*), downy brome (*Bromus tectorum*), water foxtail (*Alopecurus aequalis*), annual bluegrass (*Poa annua*), wild oat (*Avena fatua*), italian ryegrass (*Lolium multiflorum*), smartweed . (*Polygonum lapathifolium*), slender amaranth (*Amaranthus viridis*), lambsquarters (*Chenopodium album*), velvetleaf (*Abutilon theophrasti*), common cocklebur (*Xanthium strumarium*), morningglory (*Ipomoea spp*), chickweed (*Stellaria media*), prickly sida (*Sida spinosa*), sicklepod (*Cassia tora*), Japanese bindweed (*Calystegia hederacea*), wild mustard (*Brassica arvensis*), field bindweed (*Convolvulus arvensis*), jimsonweed (*Datura stramonium*), rice flatsedge (*Cyperus iria*), broadleaf signalgrass (*Brachiaria platyphylla*), wild buckwheat (*Polygonum convolvulus*) and devils beggarticks (*Bidens frondosa*), and perennial weeds such as purple nutsedge (*Cyperus rotundus*), johnsongrass (*Sorghum halepense*), bermudagrass (*Cynodon dactylon*) and quackgrass (*Agropyron repens*) grown in upland fields.

Further, they are capable of effectively controlling annual weeds such as barnyardgrass (*Echinochloa crusgalli*), flatsedge (*Cyperus difformis*), monochoria (*Monochoria vaginalis*), bulrush (*Scirpus hotarui*) and *Alisma canaliculatum*, and perennial weeds such as *Cyperus serotinus, Sagittaria pygmaea* and *Eleocharis kuroguwai*, grown in paddy fields.

On the other hand, they are highly safe to crop plants, particularly to cotton (*Gossypium indicum*) and soybean (*Glycine max*).

Now, the herbicidal activities of the herbicides of the present invention will be described with reference to Test Examples.

The following abbreviations represent the following test plants:

Ec: barnyardgrass (*Echinochloa crus-galli*)
Di: crabgrass (*Digitaria sanguinalis*)
Po: smartweed (*Polygonum lapathifolium*)
Am: slender amaranth (*Amaranthus retroflexus*)
Ch: lambsquarters (*Chenopodium album*)
Ci: rice flatsedge (*Cyperus iria*)
Cd: flatsedge (*Cyperus difformis*)
Mo: monochoria (*Monochoria vaginalis*)
Sc: bulrush (*Scirpus hotarui*)
Se: green foxtail (*Setaria viridis*)
So: Johnsongrass (*Sorghum halepense*)
Al: blackgrass (*Alopecurus myosuroides*)
Go: cotton (*Gossypium hirsutum*) and
Gl: soybean (*Glycine max*)

TEST EXAMPLE 1

In a pot filled with soil (surface area: 100 cm$^2$), seeds of barnyardgrass (Ec), crabgrass (Di), smartweed (Po), slender amaranth (Am), lambsquarters (Ch) and rice flatsedge (Ci), were sown and covered with soil in a thickness of from 0.5 to 1 cm. The pot was cultured in a green house at a temperature of from 20° to 25° C. for 2 weeks, and then a predetermined amount of a wettable powder prepared in accordance with Formulation Example 1 was diluted with water, and applied to the foliage at a rate of 100 liters per 10 ares (dose of active ingredient: 400 g/10 ares). The evaluation was conducted on the 14th day after the treatment in accordance with the standard as identified in Table 3. The results are shown by the index numbers in Table 4.

TABLE 3

| Index No. | Herbicidal effects |
| --- | --- |
| 0 | No herbicidal effect |
| 1 | Herbicidal effect: more than 0% and less than 30% |
| 2 | Herbicidal effect: at least 30% and less than 50% |
| 3 | Herbicidal effect: at least 50% and less than 70% |
| 4 | Herbicidal effect: at least 70% and less than 90% |
| 5 | Herbicidal effect: more than 90% |

TABLE 4

| Compound No. | Ec | Di | Po | Am | Ch | Ci |
| --- | --- | --- | --- | --- | --- | --- |
| 2 | 4 | 3 | 5 | 5 | 4 | 4 |
| 3 | 4 | 3 | 5 | 5 | 5 | 4 |
| 4 | 5 | 5 | 5 | 5 | 5 | 5 |
| 5 | 5 | 4 | 5 | 5 | 5 | 5 |
| 6 | 5 | 5 | 5 | 5 | 5 | 5 |
| 7 | 5 | 5 | 5 | 5 | 5 | 5 |
| 8 | 5 | 5 | 5 | 5 | 5 | 5 |
| 9 | 5 | 5 | 5 | 5 | 5 | 5 |
| 10 | 5 | 4 | 5 | 5 | 3 | 4 |
| 11 | 5 | 5 | 4 | 5 | 3 | 4 |
| 12 | 5 | 5 | 5 | 5 | 5 | 5 |
| 14 | 5 | 5 | 5 | 5 | 5 | 5 |
| 15 | 5 | 5 | 5 | 5 | 5 | 5 |
| 18 | 5 | 5 | 5 | 5 | 5 | 5 |
| 19 | 5 | 5 | 5 | 5 | 5 | 5 |
| 20 | 5 | 5 | 5 | 5 | 5 | 5 |
| 21 | 5 | 5 | 5 | 5 | 5 | 5 |
| 24 | 5 | 5 | 5 | 5 | 4 | 5 |
| 26 | 5 | 4 | 5 | 4 | 4 | 4 |

TABLE 4-continued

| Compound No. | Ec | Di | Po | Am | Ch | Ci |
| --- | --- | --- | --- | --- | --- | --- |
| 29 | 5 | 5 | 5 | 5 | 5 | 5 |
| 30 | 5 | 4 | 5 | 5 | 5 | 5 |
| 36 | 5 | 5 | 5 | 5 | 5 | 5 |
| 38 | 5 | 5 | 5 | 5 | 5 | 5 |
| 39 | 5 | 5 | 5 | 5 | 5 | 4 |
| 40 | 5 | 3 | 5 | 5 | 5 | 5 |
| 41 | 5 | 4 | 5 | 4 | 4 | 4 |
| 42 | 5 | 5 | 5 | 5 | 5 | 5 |
| 44 | 5 | 4 | 3 | 5 | 3 | 4 |
| 50 | 5 | 3 | 5 | 5 | 5 | 5 |
| 53 | 5 | 4 | 5 | 5 | 4 | 5 |
| 57 | 5 | 4 | 5 | 5 | 4 | 5 |
| 61 | 5 | 4 | 5 | 5 | 4 | 5 |
| 62 | 5 | 5 | 5 | 5 | 5 | 5 |
| 65 | 5 | 5 | 5 | 5 | 5 | 5 |
| 66 | 5 | 5 | 5 | 5 | 5 | 5 |
| 69 | 5 | 4 | 5 | 5 | 5 | 5 |
| 70 | 5 | 4 | 5 | 5 | 5 | 5 |
| 71 | 5 | 3 | 5 | 5 | 4 | 5 |
| 73 | 5 | 4 | 5 | 3 | 3 | 5 |
| 76 | 4 | 4 | 4 | 4 | 4 | 5 |
| 77 | 4 | 4 | 5 | 4 | 4 | 5 |
| 78 | 4 | 4 | 5 | 5 | 4 | 5 |
| 79 | 5 | 5 | 5 | 4 | 5 | 5 |
| 90 | 4 | 4 | 5 | 5 | 5 | 5 |
| 105 | 5 | 4 | 5 | 5 | 4 | 5 |
| 107 | 5 | 5 | 5 | 5 | 5 | 5 |
| 117 | 5 | 5 | 5 | 5 | 5 | 5 |
| 119 | 5 | 5 | 5 | 5 | 5 | 5 |
| 121 | 4 | 4 | 5 | 5 | 5 | 5 |
| 132 | 5 | 4 | 5 | 5 | 5 | 5 |
| 133 | 5 | 3 | 5 | 5 | 5 | 5 |
| 135 | 4 | 4 | 5 | 5 | 5 | 5 |
| 139 | 5 | 3 | 5 | 5 | 4 | 5 |
| 140 | 4 | 3 | 4 | 5 | 3 | 5 |
| 141 | 5 | 5 | 5 | 5 | 5 | 5 |
| 142 | 3 | 4 | 5 | 5 | 5 | 3 |
| 152 | 5 | 5 | 5 | 5 | 5 | 5 |
| 153 | 5 | 5 | 5 | 5 | 5 | 5 |
| 155 | 5 | 5 | 5 | 5 | 5 | 5 |
| 156 | 5 | 5 | 5 | 5 | 5 | 5 |
| 157 | 5 | 5 | 5 | 5 | 5 | 5 |
| 159 | 4 | 4 | 5 | 5 | 4 | 5 |
| 161 | 5 | 4 | 5 | 5 | 5 | 4 |
| 162 | 5 | 5 | 5 | 5 | 5 | 5 |
| 163 | 5 | 4 | 4 | 5 | 4 | 5 |
| 165 | 5 | 5 | 5 | 5 | 5 | 5 |
| 170 | 5 | 4 | 4 | 5 | 4 | 5 |
| 171 | 4 | 4 | 5 | 5 | 5 | 5 |
| 172 | 5 | 5 | 5 | 5 | 5 | 5 |
| 177 | 5 | 5 | 5 | 5 | 5 | 5 |
| 178 | 5 | 5 | 5 | 5 | 5 | 5 |
| 179 | 5 | 4 | 4 | 5 | 4 | 4 |
| 182 | 5 | 4 | 5 | 5 | 5 | 5 |
| 183 | 5 | 5 | 5 | 5 | 5 | 5 |
| 186 | 5 | 5 | 5 | 5 | 5 | 5 |
| 187 | 5 | 5 | 5 | 5 | 5 | 5 |
| 190 | 5 | 5 | 5 | 5 | 5 | 5 |
| 191 | 5 | 5 | 5 | 5 | 5 | 5 |
| 192 | 5 | 5 | 5 | 5 | 5 | 5 |
| 193 | 5 | 4 | 5 | 5 | 5 | 5 |
| 194 | 5 | 4 | 5 | 5 | 5 | 5 |
| 199 | 5 | 4 | 5 | 5 | 5 | 5 |
| 200 | 5 | 4 | 5 | 5 | 5 | 5 |
| 201 | 5 | 4 | 5 | 5 | 4 | 5 |
| 202 | 5 | 3 | 5 | 5 | 4 | 5 |
| 203 | 5 | 5 | 5 | 5 | 5 | 5 |
| 204 | 5 | 5 | 5 | 5 | 5 | 5 |
| 209 | 5 | 5 | 5 | 5 | 5 | 5 |
| 212 | 5 | 3 | 5 | 5 | 5 | 5 |
| 213 | 5 | 4 | 5 | 5 | 4 | 5 |
| 214 | 5 | 4 | 5 | 5 | 4 | 5 |
| 216 | 5 | 5 | 5 | 5 | 5 | 5 |
| 219 | 5 | 5 | 5 | 5 | 5 | 5 |
| 220 | 5 | 5 | 5 | 5 | 5 | 5 |
| 224 | 5 | 5 | 5 | 5 | 5 | 5 |
| 226 | 5 | 4 | 5 | 5 | 4 | 5 |
| 227 | 5 | 5 | 5 | 5 | 4 | 5 |
| 228 | 5 | 4 | 5 | 5 | 4 | 5 |

TABLE 4-continued

| Compound No. | Ec | Di | Po | Am | Ch | Ci |
| --- | --- | --- | --- | --- | --- | --- |
| 232 | 5 | 5 | 5 | 5 | 5 | 5 |
| 233 | 5 | 5 | 5 | 5 | 5 | 5 |
| 234 | 5 | 5 | 4 | 5 | 5 | 5 |
| 235 | 5 | 5 | 5 | 5 | 4 | 4 |
| 238 | 5 | 5 | 5 | 5 | 4 | 4 |
| 240 | 5 | 4 | 5 | 5 | 4 | 5 |
| 242 | 5 | 3 | 4 | 5 | 4 | 4 |
| 243 | 5 | 5 | 5 | 5 | 5 | 5 |
| 244 | 5 | 5 | 5 | 5 | 5 | 5 |
| 247 | 5 | 4 | 5 | 5 | 5 | 3 |
| 248 | 5 | 4 | 5 | 5 | 5 | 4 |
| 250 | 4 | 4 | 5 | 5 | 5 | — |
| 251 | 5 | 4 | 5 | 5 | 5 | 5 |
| 252 | 5 | 3 | 5 | 5 | 4 | 3 |
| 253 | 5 | 4 | 5 | 5 | 5 | 5 |
| 255 | 5 | 4 | 5 | 5 | 5 | 5 |
| 260 | 5 | 5 | 3 | 5 | 5 | 5 |
| 263 | 5 | 4 | 5 | 5 | 5 | 5 |
| 265 | 4 | 2 | 5 | 5 | 4 | 4 |
| 266 | 5 | 3 | 5 | 5 | 5 | 5 |
| 267 | 5 | 4 | 5 | 5 | 5 | 5 |
| 268 | 5 | 4 | 5 | 5 | 5 | 5 |
| 270 | 4 | 3 | 5 | 5 | 4 | 5 |
| 271 | 5 | 4 | 5 | 5 | 4 | 5 |
| 280 | 4 | 3 | 5 | 5 | 4 | 5 |
| 281 | 5 | 4 | 5 | 5 | 5 | 5 |
| 282 | 5 | 4 | 5 | 5 | 5 | 5 |
| 286 | 5 | 4 | 5 | 5 | 4 | 5 |
| 291 | 5 | 5 | 5 | 5 | 4 | 5 |
| 292 | 4 | — | 5 | 5 | 4 | 5 |
| 297 | 5 | 5 | 5 | 5 | 5 | 5 |
| 298 | 5 | 5 | 5 | 5 | 5 | 5 |
| 299 | 5 | 4 | 5 | 5 | 5 | 5 |
| 300 | 5 | 3 | 5 | 5 | 5 | 5 |
| 302 | 4 | — | 5 | 5 | 5 | 5 |
| 303 | 4 | 3 | 5 | 5 | 5 | 5 |
| 310 | 5 | 3 | 4 | 5 | 4 | 5 |
| 311 | 4 | — | 5 | 5 | 5 | 5 |
| 312 | 5 | 4 | 5 | 5 | 5 | 5 |
| 313 | 5 | 5 | 5 | 5 | 5 | 5 |
| 314 | 5 | 4 | 5 | 5 | 5 | 5 |
| 315 | 5 | 4 | 5 | 5 | 5 | 5 |
| 316 | 5 | 3 | 5 | 5 | 5 | 5 |
| 317 | 5 | — | 5 | 5 | 4 | 5 |
| 318 | 5 | — | 5 | 5 | 5 | 5 |
| 319 | 5 | 4 | 5 | 5 | 5 | 5 |
| 321 | — | — | 5 | 5 | 5 | 5 |
| 322 | 3 | — | 5 | 5 | 5 | 5 |
| 323 | 5 | 5 | 4 | 5 | 5 | 5 |
| 324 | 5 | 5 | 5 | 5 | 5 | 5 |
| 326 | 5 | 5 | 5 | 5 | 5 | — |
| 327 | 5 | 5 | 5 | 5 | 5 | — |
| 328 | 5 | 4 | 5 | 5 | 5 | — |
| 329 | 5 | 5 | 5 | 5 | 5 | — |
| 330 | 5 | 5 | 5 | 5 | 5 | — |
| 331 | 5 | 5 | 5 | 5 | 5 | — |
| 332 | 5 | 3 | 5 | 5 | 5 | — |
| 334 | 5 | 4 | 5 | 5 | 5 | — |
| 336 | 5 | 5 | 5 | 5 | 5 | — |
| 337 | 5 | 5 | 5 | 5 | 5 | — |
| 338 | 5 | 5 | 5 | 5 | 5 | — |
| 340 | 5 | 3 | 5 | 5 | 5 | — |
| 341 | 5 | 5 | 5 | 5 | 5 | — |
| 342 | 5 | 5 | 5 | 5 | 5 | — |
| 343 | 5 | 5 | 5 | 5 | 5 | — |
| 344 | 5 | 4 | 5 | 5 | 5 | — |
| 345 | 5 | 4 | 5 | 5 | 5 | — |
| 347 | 4 | 4 | 3 | 5 | 5 | 5 |
| 348 | 5 | 5 | 5 | 5 | 5 | — |
| 349 | 5 | 3 | 5 | 5 | — | — |
| 352 | 5 | 5 | 5 | 5 | 5 | 5 |
| 353 | 5 | 5 | 5 | 5 | 5 | — |
| 354 | 5 | 5 | 5 | 5 | 5 | — |
| 357 | 5 | 4 | 4 | 5 | 4 | 5 |
| 358 | 5 | 5 | 5 | 5 | 5 | 5 |
| 359 | 5 | 5 | 5 | 5 | 5 | 5 |
| 360 | 5 | 5 | 4 | 5 | 5 | 5 |
| 361 | 5 | 5 | 5 | 5 | 5 | 5 |
| 362 | 3 | 4 | 5 | 5 | 5 | 5 |
| 363 | 5 | 5 | 5 | 5 | 5 | 5 |
| 364 | 5 | 5 | 5 | 5 | 5 | 5 |
| 365 | 5 | 3 | 3 | 5 | 5 | 5 |
| 367 | 5 | 3 | 5 | 5 | 5 | — |
| 368 | 4 | — | 4 | 5 | 5 | 5 |
| 369 | 3 | 3 | 5 | 5 | 4 | 5 |
| 370 | 5 | — | 5 | 5 | 5 | 5 |
| 372 | 5 | 5 | 5 | 5 | 5 | 5 |
| 373 | 5 | 4 | 5 | 5 | 5 | 5 |
| 374 | 5 | 5 | 5 | 5 | 5 | 5 |
| 375 | 5 | 4 | 5 | 5 | 5 | 5 |
| 376 | 5 | — | 5 | 5 | 5 | 5 |
| 377 | 5 | 5 | 5 | 5 | 5 | 5 |
| 378 | 5 | 4 | 5 | 5 | 5 | 5 |
| 379 | 5 | 3 | 5 | 5 | 5 | 5 |
| 383 | 5 | 5 | 5 | 5 | 5 | — |
| 385 | 5 | 5 | 5 | 5 | 5 | 5 |
| 386 | 5 | 5 | 5 | 5 | 5 | 5 |
| 387 | 5 | 5 | 5 | 5 | 5 | 5 |
| 388 | 5 | 5 | 5 | 5 | 5 | 5 |
| 389 | 5 | 5 | 5 | 5 | 5 | 5 |
| 390 | 5 | 4 | 5 | 5 | 5 | 5 |
| 392 | 5 | 4 | 5 | 5 | 5 | 5 |
| 393 | 5 | 3 | 4 | 4 | 5 | 5 |
| 394 | 5 | 4 | 5 | 5 | 5 | 5 |
| 395 | 5 | 4 | 5 | 5 | 5 | — |
| 397 | 5 | 4 | 5 | 5 | 5 | 5 |
| 400 | 5 | 5 | 5 | 5 | 5 | 5 |
| 402 | 5 | 5 | 5 | 5 | 5 | 5 |
| 416 | 5 | 4 | 5 | 5 | 5 | 5 |
| 417 | 4 | 5 | 5 | 5 | 4 | 4 |

TEST EXAMPLE 2

In a pot filled with soil (surface area: 100 cm²), seeds of barnyardgrass (Ec), crabgrass (Di), smartweed (Po), slender amaranth (Am), lambsquarters (Ch) and rice flatsedge (Ci) were sown and covered with soil in a thickness of from 0.5 to 1 cm. One day later from the seeding, a predetermined amount of a wettable powder prepared in accordance with Formulation Example 1, was diluted with water and applied to the soil surface at a rate of 100 liters per 10 ares (dose of active ingredient: 400 g/10 ares). The evaluation was conducted on the 20th day after the treatment in accordance with the standard as identified in Table 3. The results are shown by the index numbers in Table 5.

TABLE 5

| Compound No. | Ec | Di | Po | Am | Ch | Ci |
| --- | --- | --- | --- | --- | --- | --- |
| 3 | 4 | 4 | 5 | 5 | 3 | 4 |
| 4 | 5 | 5 | 5 | 5 | 5 | 5 |
| 5 | 5 | 4 | 5 | 5 | 5 | 4 |
| 6 | 5 | 5 | 5 | 5 | 5 | 5 |
| 7 | 5 | 5 | 5 | 5 | 5 | 5 |
| 8 | 5 | 5 | 5 | 5 | 5 | 5 |
| 9 | 5 | 5 | 5 | 5 | 5 | 5 |
| 10 | 4 | 5 | 5 | 5 | 5 | 5 |
| 11 | 5 | 5 | 5 | 5 | 5 | 5 |
| 12 | 5 | 5 | 5 | 5 | 5 | 5 |
| 14 | 4 | 4 | 5 | 5 | 5 | 5 |
| 15 | 5 | 5 | 5 | 5 | 5 | 5 |
| 17 | 5 | 4 | 5 | 5 | 5 | 5 |
| 18 | 5 | 5 | 5 | 5 | 5 | 5 |
| 19 | 5 | 5 | 5 | 5 | 5 | 5 |
| 20 | 5 | 5 | 5 | 5 | 5 | 5 |
| 21 | 5 | 5 | 5 | 5 | 5 | 5 |
| 29 | 5 | 4 | 5 | 5 | 5 | 5 |
| 30 | 5 | 5 | 5 | 5 | 5 | 5 |
| 36 | 5 | 5 | 5 | 5 | 5 | 5 |
| 39 | 5 | 5 | 3 | 5 | 5 | 5 |
| 40 | 5 | 4 | 5 | 5 | 5 | 5 |
| 42 | 5 | 5 | 5 | 5 | 5 | 5 |

TABLE 5-continued

| Compound No. | Herbicidal effect | | | | | |
|---|---|---|---|---|---|---|
| | Ec | Di | Po | Am | Ch | Ci |
| 44 | 5 | 5 | 5 | 5 | 5 | 5 |
| 46 | 5 | 4 | 5 | 5 | 5 | 4 |
| 47 | 5 | 5 | 5 | 5 | 5 | 5 |
| 50 | 5 | 4 | 3 | 5 | 5 | 5 |
| 53 | 4 | 4 | 5 | 5 | 4 | 5 |
| 57 | 5 | 4 | 3 | 5 | 4 | 5 |
| 61 | 4 | 4 | 5 | 5 | 5 | 5 |
| 62 | 5 | 5 | 5 | 5 | 5 | 5 |
| 63 | 5 | 5 | 5 | 5 | 5 | 5 |
| 64 | 5 | 4 | 5 | 5 | 4 | 4 |
| 65 | 5 | 5 | 5 | 5 | 5 | 5 |
| 66 | 5 | 5 | 5 | 5 | 5 | 5 |
| 70 | 5 | 4 | 5 | 5 | 5 | 5 |
| 73 | 4 | 5 | 5 | 5 | 5 | 5 |
| 85 | 5 | 3 | 5 | 5 | 5 | 4 |
| 86 | 5 | 3 | 5 | 5 | 5 | 5 |
| 90 | 4 | 4 | 3 | 5 | 4 | 5 |
| 93 | 3 | 5 | 5 | 4 | 5 | 5 |
| 97 | 5 | 4 | 5 | 5 | 5 | 5 |
| 98 | 5 | 4 | 5 | 5 | 5 | 5 |
| 100 | 5 | 4 | 3 | 5 | 3 | 4 |
| 103 | 4 | 4 | 3 | 5 | 5 | 5 |
| 105 | 5 | 3 | 5 | 5 | 5 | 5 |
| 117 | 5 | 5 | 5 | 5 | 5 | 5 |
| 119 | 5 | 4 | 5 | 5 | 5 | 5 |
| 121 | 5 | 4 | 5 | 5 | 5 | 5 |
| 132 | 5 | 5 | 5 | 5 | 5 | 5 |
| 133 | 5 | 4 | 5 | 5 | 5 | 5 |
| 135 | 5 | 4 | 5 | 5 | 5 | 5 |
| 139 | 5 | 4 | 5 | 5 | 5 | 4 |
| 140 | 4 | 4 | 5 | 5 | 3 | 5 |
| 141 | 5 | 5 | 5 | 5 | 5 | 5 |
| 151 | 5 | 4 | 5 | 5 | 4 | 5 |
| 152 | 5 | 5 | 5 | 5 | 5 | 5 |
| 153 | 5 | 4 | 5 | 5 | 5 | 5 |
| 154 | 3 | 3 | 5 | 5 | 4 | 4 |
| 155 | 4 | 3 | 5 | 5 | 5 | 5 |
| 156 | 5 | 5 | 5 | 5 | 5 | 5 |
| 157 | 5 | 5 | 5 | 5 | 5 | 5 |
| 159 | 5 | 4 | 5 | 5 | 5 | 4 |
| 160 | 5 | 5 | 5 | 5 | 5 | — |
| 161 | 4 | 4 | 4 | 5 | 5 | — |
| 162 | 5 | 5 | 5 | 5 | 5 | — |
| 163 | 5 | 5 | 5 | 5 | 5 | 5 |
| 165 | 5 | 5 | 5 | 5 | 5 | 5 |
| 167 | 5 | 5 | 5 | 5 | 4 | 5 |
| 170 | 5 | 3 | 5 | 5 | 5 | 3 |
| 171 | 5 | 5 | 5 | 5 | 4 | 5 |
| 172 | 5 | 5 | 5 | 5 | 5 | 5 |
| 177 | 5 | 5 | 5 | 5 | 5 | 5 |
| 178 | 5 | 5 | 5 | 5 | 5 | 5 |
| 179 | 5 | 5 | 5 | 5 | 5 | 4 |
| 182 | 5 | 5 | 5 | 5 | 5 | 5 |
| 183 | 5 | 5 | 5 | 5 | 5 | 5 |
| 184 | 5 | 3 | 5 | 5 | 4 | 5 |
| 185 | 5 | 3 | 5 | 5 | 5 | 5 |
| 186 | 5 | 5 | 5 | 5 | 5 | 5 |
| 187 | 5 | 5 | 5 | 5 | 5 | 5 |
| 190 | 5 | 5 | 5 | 5 | 5 | 5 |
| 191 | 5 | 5 | 5 | 5 | 5 | 5 |
| 192 | 5 | 5 | 5 | 5 | 5 | 5 |
| 193 | 5 | 5 | 5 | 5 | 5 | 5 |
| 194 | 5 | 4 | 5 | 5 | 5 | 5 |
| 199 | 5 | 5 | 5 | 5 | 5 | 5 |
| 200 | 5 | 4 | 5 | 5 | 5 | 5 |
| 201 | 4 | 4 | 5 | 5 | 5 | 5 |
| 202 | 4 | 3 | 5 | 5 | 4 | 5 |
| 203 | 5 | 5 | 5 | 5 | 5 | 5 |
| 204 | 5 | 5 | 5 | 5 | 5 | 5 |
| 209 | 5 | 5 | 5 | 5 | 5 | 5 |
| 210 | 5 | 4 | 5 | 5 | 4 | 3 |
| 212 | 5 | 4 | 5 | 5 | 5 | 5 |
| 213 | 5 | 4 | 4 | 5 | 5 | 5 |
| 214 | 5 | 5 | 5 | 5 | 5 | 5 |
| 216 | 5 | 5 | 5 | 5 | 5 | 5 |
| 217 | 5 | 3 | 5 | 5 | 5 | 4 |
| 218 | 5 | 4 | 5 | 5 | 5 | 4 |
| 219 | 5 | 5 | 5 | 5 | 5 | 5 |
| 220 | 5 | 5 | 5 | 5 | 5 | 5 |
| 224 | 5 | 5 | 5 | 5 | 5 | 5 |
| 226 | 5 | 5 | 5 | 5 | 5 | 5 |
| 227 | 5 | 5 | 5 | 5 | 5 | 5 |
| 228 | 5 | 5 | 4 | 5 | 5 | 5 |
| 232 | 5 | 4 | 5 | 5 | 5 | 5 |
| 233 | 5 | 4 | 5 | 5 | 5 | 5 |
| 234 | 5 | 5 | 5 | 5 | 5 | 5 |
| 235 | 5 | 5 | 5 | 5 | 5 | 4 |
| 238 | 5 | 5 | 4 | 5 | 4 | 4 |
| 239 | 5 | 3 | 4 | 4 | 4 | 4 |
| 242 | 3 | 4 | 4 | 5 | 5 | 4 |
| 243 | 5 | 5 | 5 | 5 | 5 | 5 |
| 244 | 5 | 5 | 5 | 5 | 5 | 5 |
| 247 | 5 | 5 | 5 | 5 | 5 | 5 |
| 248 | 5 | 5 | 5 | 5 | 5 | 5 |
| 250 | 5 | 5 | 5 | 5 | 5 | 5 |
| 251 | 5 | 5 | 5 | 5 | 5 | 5 |
| 252 | 5 | 5 | 5 | 5 | 5 | 5 |
| 253 | 5 | 4 | 5 | 5 | 5 | 5 |
| 254 | 5 | 4 | 5 | 5 | 5 | 5 |
| 255 | 5 | 3 | 5 | 5 | 5 | 5 |
| 260 | 5 | 5 | 5 | 5 | 5 | 5 |
| 261 | 5 | 4 | 5 | 5 | 5 | 5 |
| 263 | 5 | 5 | 5 | 5 | 5 | 5 |
| 267 | 5 | 5 | 5 | 5 | 5 | 5 |
| 268 | 5 | 3 | 5 | 5 | 4 | 5 |
| 270 | 4 | 4 | 5 | 5 | 5 | 5 |
| 271 | 5 | 4 | 5 | 5 | 2 | 5 |
| 273 | 4 | 4 | 4 | 5 | 5 | 5 |
| 274 | 5 | — | 5 | 5 | 5 | 5 |
| 280 | 4 | — | 5 | 5 | 5 | 5 |
| 281 | 5 | 5 | 5 | 5 | 5 | 5 |
| 282 | 5 | 3 | 5 | 5 | 5 | 5 |
| 286 | 5 | 5 | 5 | 5 | 5 | 5 |
| 291 | 5 | 4 | 5 | 5 | 5 | 5 |
| 292 | 4 | 4 | 5 | 5 | 5 | 5 |
| 297 | 5 | 5 | 5 | 5 | 5 | 5 |
| 298 | 5 | 5 | 5 | 5 | 5 | 5 |
| 299 | 5 | 5 | 5 | 5 | 5 | 5 |
| 300 | 5 | 5 | 5 | 5 | 5 | 5 |
| 310 | 5 | 4 | 5 | 5 | 5 | 5 |
| 311 | 5 | 5 | 5 | 5 | 5 | 5 |
| 312 | 5 | 5 | 5 | 5 | 5 | 5 |
| 313 | 5 | 5 | 5 | 5 | 5 | 5 |
| 314 | 5 | 5 | 5 | 5 | 5 | 5 |
| 315 | 5 | 5 | 5 | 5 | 5 | 5 |
| 316 | 5 | 3 | 5 | 5 | 5 | 5 |
| 317 | 4 | — | 5 | 5 | — | 5 |
| 319 | 5 | — | 5 | 5 | 5 | 5 |
| 323 | 5 | 5 | 5 | 5 | 5 | 5 |
| 324 | 5 | 5 | 5 | 5 | 5 | 5 |
| 326 | 5 | 5 | 5 | 5 | 5 | 5 |
| 329 | 5 | 4 | 5 | 5 | 4 | 4 |
| 330 | 5 | 5 | 5 | 5 | 5 | 5 |
| 331 | 5 | 5 | 5 | 5 | 5 | 5 |
| 336 | 5 | 5 | 5 | 5 | 5 | 5 |
| 337 | 5 | 5 | 5 | 5 | 4 | 5 |
| 338 | 5 | 5 | 5 | 5 | 5 | 5 |
| 341 | 5 | 5 | 5 | 5 | 5 | — |
| 342 | 5 | 5 | 5 | 5 | 5 | — |
| 343 | 5 | 5 | 5 | 5 | 5 | 5 |
| 344 | 4 | 4 | 5 | 5 | 4 | 5 |
| 345 | 4 | 3 | 5 | 5 | 4 | 5 |
| 348 | 5 | 5 | 5 | 5 | 5 | 5 |
| 352 | 5 | 5 | 5 | 5 | 5 | 5 |
| 353 | 5 | 5 | 5 | 5 | 5 | 5 |
| 356 | — | — | 5 | 5 | 5 | 5 |
| 357 | 5 | 4 | 5 | 5 | 4 | 5 |
| 358 | 5 | 5 | 5 | 5 | 5 | 5 |
| 359 | 5 | 5 | 5 | 5 | 5 | 5 |
| 360 | 5 | 3 | 5 | 5 | 4 | 5 |
| 361 | 5 | 5 | 5 | 5 | 5 | 5 |
| 362 | 4 | 4 | 5 | 5 | 4 | 5 |
| 363 | 5 | 4 | 5 | 5 | 5 | 5 |
| 364 | 5 | 4 | 4 | 5 | 5 | 5 |
| 367 | 5 | 3 | 5 | 5 | 5 | 5 |
| 370 | 5 | — | 5 | 5 | 4 | 5 |
| 372 | 5 | 4 | 5 | 5 | 5 | 5 |
| 373 | 5 | 4 | 5 | 5 | 5 | 5 |

TABLE 5-continued

| Compound No. | Herbicidal effect | | | | | |
|---|---|---|---|---|---|---|
| | Ec | Di | Po | Am | Ch | Ci |
| 376 | 5 | 5 | 5 | 5 | 5 | 5 |
| 377 | 5 | 4 | 5 | 5 | 5 | 5 |
| 378 | 5 | 5 | 5 | 5 | 5 | 5 |
| 379 | 4 | 3 | 5 | 5 | 5 | 5 |
| 384 | — | — | 5 | 5 | 5 | 4 |
| 385 | 5 | 5 | 5 | 5 | 5 | 5 |
| 386 | 5 | 5 | 5 | 5 | 5 | 5 |
| 387 | 5 | 5 | 5 | 5 | 5 | 5 |
| 388 | 5 | 5 | 5 | 5 | 5 | 5 |
| 389 | 5 | 5 | 5 | 5 | 5 | 5 |
| 390 | 5 | 4 | 5 | 5 | 5 | 5 |
| 392 | 5 | 4 | 5 | 5 | 5 | 5 |
| 393 | 5 | 3 | 5 | 5 | 5 | 5 |
| 394 | 5 | 4 | 5 | 5 | 5 | 5 |
| 395 | 4 | 5 | 4 | 5 | 5 | 4 |
| 398 | 4 | 3 | 5 | 5 | 5 | 5 |
| 399 | 5 | 3 | 5 | 5 | 3 | 5 |
| 400 | 5 | 5 | 5 | 5 | 5 | 5 |
| 402 | 5 | 5 | 5 | 5 | 5 | 5 |
| 416 | 5 | 5 | 5 | 5 | 5 | 5 |
| 417 | 4 | 5 | 5 | 5 | 5 | 5 |

TEST EXAMPLE 3

In a pot filled with paddy field soil (surface area: 100 cm$^2$), seeds of barnyardgrass (Ec), flatsedge (Cd), monochoria (Mo) and bulrush (Sc) were sown, and water was introduced to a depth of 5 cm. Two days later from the seeding, a predetermined amount of wettable powder prepared in accordance with Formulation Example 1, was diluted with water and dropwise applied to the water surface in a dose of 100 g of the active ingredient per 10 ares. The evaluation was conducted on the 21st day after the treatment in accordance with the standard as identified in Table 3. The results are shown by the index numbers in Table 6.

TABLE 6

| Compound No. | Herbicidal effect | | | |
|---|---|---|---|---|
| | Ec | Cd | Mo | Sc |
| 2 | 5 | 5 | 5 | 5 |
| 4 | 5 | 5 | 5 | 5 |
| 5 | 5 | 5 | 5 | 5 |
| 6 | 5 | 5 | 5 | 5 |
| 7 | 5 | 5 | 5 | 5 |
| 8 | 5 | 5 | 5 | 5 |
| 9 | 5 | 5 | 5 | 5 |
| 10 | 5 | 4 | 5 | 5 |
| 10 | 5 | 5 | 5 | 5 |
| 11 | 5 | 5 | 5 | 5 |
| 12 | 5 | 5 | 5 | 5 |
| 14 | 5 | 5 | 5 | 5 |
| 15 | 5 | 5 | 5 | 5 |
| 18 | 5 | 5 | 5 | 5 |
| 19 | 5 | 5 | 5 | 5 |
| 20 | 5 | 5 | 5 | 5 |
| 21 | 5 | 5 | 5 | 5 |
| 22 | 4 | 5 | 5 | 4 |
| 23 | 4 | 5 | 5 | 4 |
| 24 | 5 | 5 | 5 | 5 |
| 25 | 5 | 4 | 5 | 5 |
| 27 | 5 | 4 | 5 | 5 |
| 29 | 5 | 5 | 5 | 5 |
| 30 | 5 | 5 | 5 | 5 |
| 31 | 4 | 4 | 5 | 5 |
| 32 | 5 | 5 | 5 | 5 |
| 36 | 5 | 5 | 5 | 5 |
| 37 | 5 | 5 | 5 | 5 |
| 38 | 5 | 5 | 5 | 5 |
| 39 | 5 | 5 | 5 | 5 |
| 40 | 5 | 5 | 5 | 5 |
| 41 | 5 | 5 | 5 | 5 |
| 42 | 5 | 5 | 5 | 5 |
| 43 | 5 | 5 | 5 | 5 |
| 44 | 5 | 5 | 5 | 5 |
| 45 | 5 | 5 | 5 | 4 |
| 46 | 5 | 5 | 5 | 5 |
| 47 | 5 | 5 | 5 | 5 |
| 48 | 5 | 5 | 5 | 4 |
| 50 | 5 | 5 | 5 | 5 |
| 53 | 5 | 5 | 5 | 5 |
| 57 | 5 | 5 | 5 | 5 |
| 61 | 5 | 5 | 5 | 5 |
| 62 | 5 | 5 | 5 | 5 |
| 63 | 5 | 5 | 5 | 5 |
| 65 | 5 | 5 | 5 | 5 |
| 66 | 5 | 5 | 5 | 5 |
| 67 | 4 | 5 | 5 | 5 |
| 69 | 5 | 5 | 5 | 5 |
| 70 | 5 | 5 | 5 | 5 |
| 71 | 5 | 5 | 5 | 5 |
| 72 | 5 | 5 | 5 | 5 |
| 73 | 5 | 5 | 5 | 5 |
| 74 | 5 | 5 | 5 | 5 |
| 75 | 5 | 5 | 5 | 4 |
| 78 | 5 | 5 | 5 | 5 |
| 79 | 4 | 4 | 5 | 4 |
| 86 | 5 | 5 | 5 | 4 |
| 87 | 4 | 5 | 5 | 4 |
| 88 | 5 | 5 | 5 | 4 |
| 90 | 5 | 5 | 5 | 5 |
| 93 | 5 | 5 | 5 | 5 |
| 95 | 5 | 5 | 5 | 5 |
| 98 | 5 | 5 | 5 | 5 |
| 100 | 5 | 5 | 5 | 5 |
| 103 | 5 | 5 | 5 | 5 |
| 105 | 5 | 5 | 5 | 5 |
| 106 | 4 | 5 | 5 | 5 |
| 109 | 5 | 5 | 5 | 5 |
| 111 | 5 | 5 | 5 | 4 |
| 117 | 5 | 5 | 5 | 5 |
| 118 | 5 | 5 | 5 | 5 |
| 119 | 5 | 5 | 5 | 5 |
| 121 | 5 | 5 | 5 | 5 |
| 132 | 5 | 5 | 5 | 5 |
| 133 | 5 | 5 | 5 | 5 |
| 135 | 5 | 5 | 5 | 5 |
| 136 | 5 | 4 | 5 | 5 |
| 137 | 4 | 5 | 5 | 5 |
| 139 | 5 | 5 | 5 | 5 |
| 140 | 5 | 5 | 5 | 5 |
| 141 | 5 | 5 | 5 | 5 |
| 142 | 5 | 5 | 5 | 5 |
| 143 | 5 | 5 | 5 | 5 |
| 144 | 4 | 5 | 5 | 5 |
| 151 | 5 | 5 | 5 | 5 |
| 152 | 5 | 5 | 5 | 5 |
| 153 | 5 | 5 | 5 | 5 |
| 155 | 5 | 5 | 5 | 5 |
| 156 | 5 | 5 | 5 | 5 |
| 157 | 5 | 5 | 5 | 5 |
| 159 | 5 | 5 | 5 | 4 |
| 160 | 5 | 4 | 5 | 5 |
| 161 | 5 | 5 | 5 | 5 |
| 162 | 5 | 5 | 5 | 5 |
| 165 | 5 | 5 | 5 | 5 |
| 167 | 5 | 5 | 5 | 5 |
| 169 | 4 | 5 | 5 | 5 |
| 170 | 5 | 5 | 5 | 5 |
| 171 | 5 | 5 | 5 | 5 |
| 172 | 5 | 5 | 5 | 5 |
| 174 | 4 | 5 | 5 | 4 |
| 177 | 5 | 5 | 5 | 5 |
| 178 | 5 | 5 | 5 | 5 |
| 179 | 5 | 5 | 5 | 5 |
| 182 | 5 | 5 | 5 | 5 |
| 183 | 5 | 5 | 5 | 5 |
| 184 | 5 | 5 | 5 | 5 |
| 185 | 5 | 5 | 5 | 5 |
| 186 | 5 | 5 | 5 | 5 |
| 187 | 5 | 5 | 5 | 5 |
| 190 | 5 | 5 | 5 | 5 |
| 191 | 5 | 5 | 5 | 5 |

TABLE 6-continued

| Compound No. | Herbicidal effect | | | | Compound No. | Herbicidal effect | | | |
|---|---|---|---|---|---|---|---|---|---|
| | Ec | Cd | Mo | Sc | | Ec | Cd | Mo | Sc |
| 192 | 5 | 5 | 5 | 5 | 314 | 5 | 5 | 5 | 5 |
| 193 | 5 | 5 | 5 | 5 | 315 | 5 | 5 | 5 | 5 |
| 194 | 5 | 5 | 5 | 5 | 316 | 5 | 5 | 5 | 5 |
| 199 | 5 | 5 | 5 | 5 | 317 | 5 | 5 | 5 | 5 |
| 200 | 5 | 5 | 5 | 5 | 318 | 5 | 5 | 5 | 5 |
| 201 | 4 | 4 | 5 | 5 | 319 | 5 | 5 | 5 | 5 |
| 202 | 3 | 5 | 5 | 5 | 320 | 3 | 5 | 5 | 5 |
| 203 | 5 | 5 | 5 | 5 | 321 | 3 | 5 | 5 | 4 |
| 204 | 5 | 5 | 5 | 5 | 322 | 4 | 5 | 5 | 5 |
| 206 | 3 | 5 | 5 | 5 | 323 | 5 | 5 | 5 | 5 |
| 209 | 5 | 5 | 5 | 5 | 324 | 5 | 5 | 5 | 5 |
| 210 | 5 | 5 | 5 | 5 | 325 | 5 | 5 | 5 | 4 |
| 211 | 5 | 5 | 5 | 5 | 326 | 5 | 5 | 5 | 5 |
| 212 | 5 | 5 | 5 | 5 | 327 | 5 | 5 | 5 | 5 |
| 213 | 5 | 5 | 5 | 5 | 328 | 5 | 5 | 5 | 5 |
| 214 | 5 | 5 | 5 | 5 | 329 | 5 | 5 | 5 | 5 |
| 216 | 5 | 5 | 5 | 5 | 330 | 5 | — | 5 | 5 |
| 217 | 5 | 5 | 5 | 5 | 331 | 5 | — | 5 | 5 |
| 218 | 5 | 5 | 5 | 5 | 332 | 4 | — | 5 | 5 |
| 219 | 5 | 5 | 5 | 5 | 334 | 5 | — | 5 | 5 |
| 220 | 5 | 5 | 5 | 5 | 336 | 5 | — | 5 | 5 |
| 221 | 5 | 5 | 5 | 4 | 338 | 5 | — | 5 | 5 |
| 222 | 5 | 4 | 5 | 4 | 341 | 5 | — | 5 | 5 |
| 224 | 5 | 5 | 5 | 5 | 342 | 5 | — | 5 | 5 |
| 225 | 5 | 3 | 4 | 4 | 343 | 5 | — | 5 | 5 |
| 226 | 5 | 5 | 5 | 5 | 344 | 5 | — | 5 | 5 |
| 227 | 5 | 5 | 5 | 5 | 345 | 5 | — | 5 | 5 |
| 228 | 5 | 5 | 5 | 5 | 348 | 5 | — | 5 | 5 |
| 229 | 4 | 5 | 5 | 4 | 349 | 4 | — | 5 | 5 |
| 231 | 3 | 5 | 5 | 5 | 350 | 5 | — | 5 | 5 |
| 232 | 5 | 5 | 5 | 5 | 351 | 4 | — | 5 | 5 |
| 233 | 5 | 5 | 5 | 5 | 352 | 5 | — | 5 | 5 |
| 234 | 5 | 5 | 5 | 5 | 353 | 5 | — | 5 | 4 |
| 238 | 5 | 4 | 5 | 4 | 354 | 5 | — | 5 | 5 |
| 239 | 5 | 5 | 5 | 3 | 355 | 3 | — | 5 | 4 |
| 240 | 5 | 5 | 5 | 5 | 356 | 2 | 5 | 5 | 4 |
| 243 | 5 | 5 | 5 | 5 | 358 | 5 | 5 | 5 | 5 |
| 244 | 5 | 5 | 5 | 5 | 359 | 5 | 5 | 5 | 5 |
| 246 | 5 | 5 | 5 | 5 | 360 | 5 | 5 | 5 | 5 |
| 247 | 5 | 5 | 5 | 5 | 361 | 4 | 5 | 5 | 5 |
| 248 | 5 | 5 | 5 | 5 | 362 | 4 | 5 | 5 | 5 |
| 250 | 5 | 5 | 5 | 5 | 363 | 5 | — | 5 | 5 |
| 251 | 5 | 5 | 5 | 5 | 364 | 5 | — | 5 | 5 |
| 252 | 5 | 5 | 5 | 5 | 365 | 5 | 5 | 5 | 5 |
| 253 | 5 | 5 | 5 | 5 | 366 | 5 | 5 | 5 | 5 |
| 254 | 5 | 5 | 5 | 5 | 367 | 5 | 5 | 5 | 5 |
| 255 | 5 | 5 | 5 | 5 | 368 | 4 | 5 | 5 | 5 |
| 256 | 3 | 4 | 5 | 4 | 370 | 5 | 5 | 5 | 5 |
| 259 | 3 | 4 | 4 | 4 | 371 | 5 | 5 | 5 | 5 |
| 260 | 5 | 5 | 5 | 5 | 372 | 4 | 5 | 5 | 4 |
| 261 | 5 | 5 | 5 | 5 | 373 | 5 | 5 | 5 | 5 |
| 262 | 4 | 5 | 5 | 5 | 374 | 5 | 5 | 5 | 5 |
| 263 | 5 | 5 | 5 | 5 | 375 | 5 | 5 | 5 | 5 |
| 264 | 4 | 3 | 4 | 5 | 376 | 5 | 5 | 5 | 4 |
| 266 | 4 | 4 | 5 | 5 | 377 | 5 | 5 | 5 | 5 |
| 267 | 5 | 5 | 5 | 5 | 378 | 5 | 5 | 5 | 4 |
| 268 | 5 | 5 | 5 | 5 | 382 | 3 | — | 4 | 5 |
| 270 | 4 | 5 | 5 | 4 | 383 | 5 | — | 5 | 5 |
| 271 | 4 | 5 | 5 | 4 | 385 | 5 | 5 | 5 | 5 |
| 274 | 5 | 5 | 5 | 3 | 386 | 5 | 5 | 5 | 5 |
| 280 | 5 | 5 | 5 | 5 | 387 | 5 | 5 | 5 | 5 |
| 281 | 5 | 5 | 5 | 5 | 388 | 5 | 5 | 5 | 5 |
| 282 | 5 | 5 | 5 | 5 | 389 | 5 | 5 | 5 | 5 |
| 284 | 3 | 5 | 5 | 3 | 390 | 5 | 5 | 5 | 5 |
| 286 | 5 | 5 | 5 | 5 | 391 | 5 | 5 | 5 | 5 |
| 291 | 5 | 5 | 5 | 5 | 392 | 5 | 5 | 5 | 5 |
| 292 | 5 | 5 | 5 | 5 | 393 | 5 | 5 | 5 | 5 |
| 297 | 5 | 5 | 5 | 5 | 394 | 5 | 5 | 5 | 5 |
| 298 | 5 | 5 | 5 | 5 | 395 | 5 | 5 | 5 | 5 |
| 299 | 5 | 5 | 5 | 5 | 396 | 5 | — | 5 | 5 |
| 300 | 5 | 5 | 5 | 5 | 397 | 5 | — | 5 | 5 |
| 302 | 4 | 5 | 5 | 5 | 400 | 5 | — | 5 | 5 |
| 303 | 5 | 5 | 5 | 5 | 401 | 4 | — | 5 | 3 |
| 307 | 5 | 5 | 5 | 5 | 402 | 5 | — | 5 | 5 |
| 308 | 5 | 5 | 3 | 5 | 416 | 5 | 5 | 5 | 5 |
| 310 | 5 | 5 | 5 | 5 | 417 | 5 | 5 | 5 | 5 |
| 311 | 5 | 5 | 5 | 5 | 418 | 5 | 5 | 5 | 5 |
| 312 | 5 | 5 | 5 | 5 | | | | | |
| 313 | 5 | 5 | 5 | 5 | | | | | |

TEST EXAMPLE 4

In a pot filled with soil (surface area: 600 cm$^2$), seeds of barnyardgrass (Ec), green foxtail (Se), Johnsongrass (So), blackgrass (Al), smartweed (Po), slender amaranth (Am), lambsquarters (Ch) and cotton (Go) were sown and covered with soil in a thickness of from 0.5 to 1 cm. Two days later from the seeding, a predetermined amount of a wettable powder prepared in accordance with Formulation Example 1 was diluted with water, and applied to the soil surface at a rate of 100 liters per 10 ares. The evaluation of the herbicidal effect was conducted on the 20th day after the treatment in accordance with the standard as identified in Table 3, and the evaluation of the phytotoxicity was conducted in accordance with the standard as identified in Table 7. The results are shown by the index numbers in Table 8.

TABLE 7

| Index No. | Herbicidal effects |
|---|---|
| 0 | No phytotoxicity |
| 1 | Phytotoxicity: more than 0% and less than 30% |
| 2 | Phytotoxicity: at least 30% and less than 50% |
| 3 | Phytotoxicity: at least 50% and less than 70% |
| 4 | Phytotoxicity: at least 70% and less than 90% |
| 5 | Phytotoxicity: more than 90% |

TABLE 8

| Compound No. | Dose (g · ai/10a) | Ec | Se | So | Po | Am | Ch | Phytotoxicity Go |
|---|---|---|---|---|---|---|---|---|
| 4 | 25 | 5 | 5 | 5 | 5 | 5 | 5 | 0 |
| 7 | 400 | 4 | 4 | 5 | 5 | 5 | 5 | 1 |
| 9 | 25 | 5 | 5 | 5 | 5 | 5 | 5 | 0 |
| 11 | 100 | 4 | 5 | 5 | 5 | 5 | 5 | 0 |
| 12 | 25 | 4 | 5 | 5 | 5 | 5 | 5 | 1 |
| 15 | 400 | 5 | 5 | 5 | 5 | 5 | 5 | 0 |
| 18 | 100 | 4 | 4 | 4 | 5 | 5 | 5 | 1 |
| 19 | 100 | 5 | 3 | 4 | 5 | 5 | 5 | 0 |
| 20 | 100 | 4 | 4 | 4 | 5 | 5 | 5 | 0 |
| 21 | 100 | 5 | 5 | 5 | 5 | 5 | 5 | 0 |
| 30 | 25 | 4 | 5 | 4 | 5 | 5 | 5 | 1 |
| 36 | 25 | 5 | 5 | 5 | 5 | 5 | 5 | 0 |
| 37 | 25 | 5 | 4 | 5 | 5 | 4 | 5 | 0 |
| 42 | 25 | 5 | 5 | 5 | 5 | 5 | 5 | 1 |
| 65 | 25 | 5 | 4 | 5 | 5 | 5 | 5 | 1 |
| 66 | 25 | 5 | 4 | 5 | 5 | 5 | 5 | 0 |
| 152 | 25 | 5 | 5 | 5 | 5 | 5 | 5 | 1 |
| 156 | 6.3 | 5 | 3 | 5 | 5 | 5 | 5 | 0 |
| 161 | 100 | 4 | 5 | 5 | 5 | 5 | 5 | 0 |
| 162 | 25 | 5 | 5 | 5 | 5 | 5 | 5 | 1 |
| 177 | 100 | 5 | 4 | 5 | 5 | 5 | 5 | 0 |
| 183 | 100 | 4 | 4 | 5 | 5 | 5 | 4 | 1 |
| 186 | 100 | 5 | 5 | 5 | 5 | 5 | 5 | 0 |
| 187 | 100 | 5 | 5 | 5 | 5 | 5 | 5 | 1 |
| 190 | 25 | 5 | 5 | 5 | 5 | 5 | 5 | 0 |
| 191 | 25 | 5 | 5 | 5 | 5 | 5 | 5 | 1 |
| 192 | 100 | 5 | 4 | 5 | 5 | 5 | 4 | 0 |
| 219 | 6.3 | 4 | 4 | 5 | 5 | 5 | 5 | 1 |
| 281 | 25 | 5 | 4 | 5 | 5 | 5 | 5 | 0 |
| 297 | 25 | 5 | 5 | 5 | 5 | 5 | 5 | 1 |
| 298 | 6.3 | 5 | 4 | 5 | 5 | 5 | 5 | 1 |
| 310 | 25 | 5 | 4 | 5 | 5 | 5 | 5 | 1 |
| 311 | 100 | 5 | 5 | 5 | 5 | 5 | 5 | 0 |
| 313 | 6.3 | 5 | 5 | 5 | 3 | 5 | 5 | 0 |
| 316 | 100 | 5 | 5 | 5 | 5 | 5 | 5 | 1 |
| 323 | 25 | 5 | 5 | 5 | 5 | 5 | 5 | 1 |
| 324 | 25 | 5 | 5 | 5 | 5 | 5 | 5 | 0 |
| 327 | 100 | 5 | — | 5 | 5 | 5 | 5 | 1 |
| 328 | 100 | 5 | — | 5 | 5 | 5 | 5 | 0 |
| 329 | 25 | 5 | 5 | 5 | 5 | 5 | 5 | 0 |
| 341 | 6.3 | 5 | 4 | — | 5 | 5 | 5 | 1 |
| 352 | 6.3 | 5 | 5 | 4 | 5 | 5 | 5 | 1 |
| 374 | 25 | 5 | 4 | 5 | 5 | 5 | 5 | 1 |
| 375 | 100 | 5 | 5 | 5 | 5 | 5 | 5 | 0 |
| 376 | 25 | 5 | 4 | 5 | 5 | 5 | 5 | 0 |
| 377 | 100 | 5 | 5 | 5 | 5 | 5 | 5 | 0 |
| 378 | 100 | 5 | 5 | 5 | 5 | 5 | 5 | 0 |
| 385 | 6.3 | 5 | 4 | 5 | 5 | 5 | 4 | 0 |
| 386 | 25 | 5 | 4 | 5 | 5 | 5 | 5 | 0 |
| 387 | 25 | 5 | 5 | 5 | 5 | 5 | 5 | 1 |
| 390 | 25 | 5 | 5 | 5 | 5 | 5 | 5 | 1 |
| 395 | 100 | 5 | 4 | 5 | 5 | 5 | 5 | 1 |

TEST EXAPLE 5

Tests were conducted in the same manner as in Test Example 4 except that the crop plant was changed to soybean (Gl). The results are shown by the index numbers in Table 9.

TABLE 9

| Compound No. | Dose (g · ai/10a) | Ec | Se | So | Po | Am | Ch | Phytotoxicity Gl |
|---|---|---|---|---|---|---|---|---|
| 183 | 25 | 4 | 4 | 5 | 5 | 5 | 4 | 0 |
| 185 | 100 | 4 | 4 | 5 | 4 | 5 | 3 | 0 |
| 186 | 100 | 5 | 5 | 5 | 5 | 5 | 5 | 0 |
| 187 | 100 | 5 | 4 | 5 | 5 | 5 | 5 | 1 |
| 191 | 25 | 5 | 5 | 5 | 5 | 5 | 5 | 1 |
| 192 | 100 | 5 | 4 | 5 | 5 | 5 | 4 | 0 |
| 199 | 100 | 5 | 5 | 5 | 5 | 5 | 5 | 0 |
| 224 | 25 | 4 | 5 | 5 | 5 | 5 | 5 | 1 |
| 281 | 25 | 5 | 4 | 5 | 5 | 5 | 5 | 0 |
| 292 | 25 | 5 | 4 | 5 | 5 | 5 | 5 | 1 |
| 314 | 6.3 | 5 | 4 | 5 | 5 | 5 | 5 | 1 |
| 315 | 6.3 | 5 | 4 | 4 | 5 | 5 | 5 | 1 |
| 316 | 100 | 5 | 5 | 5 | 5 | 5 | 5 | 1 |
| 324 | 25 | 4 | 4 | 5 | 5 | 5 | 5 | 0 |
| 326 | 6.3 | 5 | 5 | 5 | 5 | 5 | 5 | 1 |
| 328 | 100 | 5 | — | 5 | 5 | 5 | 5 | 0 |
| 329 | 25 | 5 | 5 | 5 | 5 | 5 | 5 | 1 |
| 343 | 25 | 5 | 5 | 5 | 5 | 5 | 4 | 1 |
| 352 | 6.3 | 5 | 5 | 4 | 5 | 5 | 5 | 0 |
| 363 | 25 | 5 | 5 | — | 5 | 5 | 5 | 0 |
| 374 | 25 | 5 | 4 | 5 | 5 | 5 | 5 | 1 |
| 385 | 6.3 | 5 | 5 | 5 | 5 | 5 | 4 | 0 |
| 386 | 6.3 | 5 | 4 | 5 | 5 | 5 | 5 | 0 |
| 390 | 25 | 5 | 5 | 5 | 5 | 5 | 5 | 1 |
| 395 | 100 | 5 | 4 | 5 | 5 | 5 | 5 | 1 |

We claim:

1. An alkanoic acid derivative of the formula:

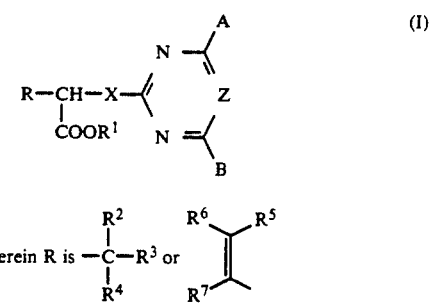

wherein R is $$-\underset{R^4}{\overset{R^2}{\underset{|}{C}}}-R^3 \quad \text{or} \quad \overset{R^6}{\underset{R^7}{\diagup}}\overset{R^5}{\diagdown}$$

wherein R$^3$ is a hydrogen atom, a halogen atom, a halogen-substituted C$_1$–C$_4$ alkyl group, a C$_1$–C$_{15}$ alkyl group, a C$_3$–C$_6$ cycloalkyl group, a C$_1$–C$_4$-alkylthio-C$_1$–C$_4$-alkyl group, a hydroxy-C$_1$–C$_4$-alkyl group, a hydroxyl group, a cyano group, a thienyl group, a naphthyl group, a dihydronaphthyl group, a C$_1$–C$_4$-alkanoyloxy-C$_1$–C$_4$-alkyl group, a benzoyloxy-C$_1$–C$_4$-alkyl group, or or —(CH$_2$)$_m$— 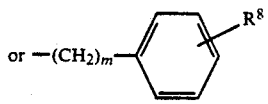

wherein R$^8$ is a hydrogen atom, a halogen atom, a nitro group, a C$_1$–C$_4$ alkyl group, a C$_1$–C$_4$ alkoxy group or —SO(O)$_n$R$^9$ group, wherein R$^9$ is a C$_1$–C$_4$ alkyl group, and n is an integer of from 0 to 2, m is an integer of from 0 to 2, each of R$^2$ and R$^4$, which may be the same or different, is a hydrogen atom or a C$_1$–C$_4$ alkyl group, or R$^2$ and R$^4$ form together with the adjacent carbon atom a 3-, 4-, 5- or 6-membered ring which may contain an oxygen atom and may be substituted by one or two C$_1$–C$_4$ alkyl groups, each of R$^5$ and R$^6$ which may be the same or different is a hydrogen atom or a C$_1$–C$_4$ alkyl group, R$^7$ is a C$_1$–C$_4$ alkyl group or a phenyl group, or R$^6$ and R$^7$ form —(CH$_2$)l— wherein l is an integer of 3 or 4 which may be substituted by one to two C$_1$–C$_4$ alkyl groups, or R is a C$_2$–C$_6$ alkenyl group, a dihydronaphthyl group, a tetrahydronaphthyl group, a 1-oxo-1,2,3,4-tetrahydronaphthyl group, a 1,2-epoxy-C$_3$–C$_6$-cycloalkyl group or an indanyl group which may be substituted by a C$_1$–C$_4$ alkyl or C$_1$–C$_4$ alkoxy group; R$^1$ is a hydrogen atom, a C$_1$–C$_4$ alkyl group, a C$_2$–C$_6$ alkenyl group, a C$_2$–C$_6$ alkynyl group, a phenyl group, a C$_1$–C$_4$ alkylideneamino group, a C$_1$–C$_4$ alkoxy-C$_1$–C$_4$-alkyl group, a C$_1$–C$_4$-alkoxycarbonyl-C$_1$–C$_4$-alkyl group, a halogen-substituted C$_1$–C$_4$ alkyl group, a C$_3$–C$_5$ cycloalkyl group, a nitro-substituted phenylthio-C$_1$–C$_4$-alkyl group, a halogen atom or a benzyl group which may be substituted by a C$_1$–C$_4$ alkyl or C$_1$–C$_4$ alkoxy group; or R and R$^1$ together form ethylene or methyl-substituted ethylene; A is a C$_1$–C$_4$ alkyl group, a C$_1$–C$_4$ alkoxy group, a C$_1$–C$_4$ alkythio group, a halogen atom, a halogen-substituted C$_1$–C$_4$ alkoxy group or a di-C$_1$–C$_4$-alkylamino group; B is a hydrogen atom, a C$_1$–C$_4$ alkyl group, a C$_1$–C$_4$ alkoxy group or a halogen-substituted C$_1$–C$_4$ alkoxy group; X is an oxygen atom or a sulfur atom; and Z is nitrogen; and a salt thereof.

2. The alkanoic acid derivative of the formula I according to claim 1, wherein R is a straight chain or branched C$_3$–C$_5$ alkyl group, a cyclopentyl group, an α-methylbenzyl group or an α,α-dimethylbenzyl group; R$^1$ is a hydrogen atom or a C$_1$–C$_4$ alkyl group; each of A and B which may be the same or different is an alkyl group or an alkoxy group; and X and Z are as defined in claim 1 and a salt thereof.

3. The alkanoic acid derivative of the formula I according to claim 1, wherein R is a straight chain or branched C$_3$–C$_5$ alkyl group, a C$_3$–C$_6$ cycloalkyl group or

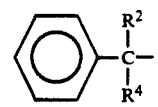

wherein each of R$^2$ and R$^4$ which may be the same or different is a hydrogen atom or a C$_1$–C$_4$ alkyl group; R$^1$ is a hydrogen atom or a C$_1$–C$_4$ alkyl group; each of A and B which may be the same or different is a C$_1$–C$_4$ alkyl group; a C$_1$–C$_4$ alkoxy group or a dihalo-C$_1$–C$_4$-alkoxy group; and X and Z are as defined in claim 1; and a salt thereof.

4. A compound according to claim 1, wherein each of A and B is a methoxy group.

5. A compound of claim 1 wherein X is oxygen.

6. The alkanoic acid derivative of the formula I according to claim 1, wherein each of A and B is a methoxy group, R is an isopropyl group, a tert-butyl group, a cyclopentyl group or an α,α-dimethylbenzyl group; R$^1$ is a hydrogen atom, a methyl group or an ethyl group; and X and Z are as defined in claim 1, and a salt thereof.

7. The alkanoic acid derivative of the formula I according to claim 1, wherein each of A and B is a methyl group, R is a C$_3$–C$_5$ alkyl group, and R$^1$, X and Z are as defined in claim 1; and a salt thereof.

8. A herbicidal composition comprising a herbicidally effective amount of an alkanoic acid derivative of the formula I or its salt as defined in claim 1, and an agricultural adjuvant.

9. A method for killing weeds which comprises applying a herbicidally effective amount of an alkanoic acid derivative of the formula I or its salt as defined in claim 1 to a locus to be protected.

* * * * *